United States Patent
Shaw et al.

(10) Patent No.: US 7,584,649 B2
(45) Date of Patent: Sep. 8, 2009

(54) SENSOR WITH MICROELECTRO-MECHANICAL OSCILLATORS

(75) Inventors: Steven W. Shaw, Williamston, MI (US);
Jeffrey F Rhoads, Charlotte, MI (US);
Barry E DeMartini, Santa Barbara, CA (US); Kimberly L Turner, Goleta, CA (US)

(73) Assignees: Board of Trustees of Michigan State University, East Lansing, MI (US); The Regents of the University of California, Oakland, CA (US)

( * ) Notice: Subject to any disclaimer, the term of this patent is extended or adjusted under 35 U.S.C. 154(b) by 105 days.

(21) Appl. No.: 11/809,803

(22) Filed: Jun. 1, 2007

(65) Prior Publication Data

US 2008/0110247 A1    May 15, 2008

Related U.S. Application Data

(60) Provisional application No. 60/810,783, filed on Jun. 2, 2006.

(51) Int. Cl.
*G01N 29/036* (2006.01)
*G01N 29/36* (2006.01)

(52) U.S. Cl. .............. 73/31.06; 73/24.06; 73/31.05; 73/61.71; 73/64.53

(58) Field of Classification Search ..... 73/24.01–24.06, 73/28.01–28.04, 31.01–31.05, 61.71, 61.75, 73/64.53
See application file for complete search history.

(56) References Cited

U.S. PATENT DOCUMENTS

| | | | |
|---|---|---|---|
| 6,250,156 B1 * | 6/2001 | Seshia et al. ............. | 73/504.12 |
| 6,260,408 B1 * | 7/2001 | Vig et al. ................. | 73/64.53 |
| 6,389,877 B1 * | 5/2002 | Takeuchi et al. .......... | 73/19.03 |
| 6,742,389 B2 * | 6/2004 | Nguyen et al. ........... | 73/504.12 |
| 7,043,985 B2 * | 5/2006 | Ayazi et al. .............. | 73/504.04 |
| 7,142,075 B1 * | 11/2006 | Roesler et al. ............ | 335/78 |
| 7,251,982 B2 * | 8/2007 | Booker ..................... | 73/24.03 |
| 7,275,433 B2 * | 10/2007 | Caminada et al. ........ | 73/514.18 |
| 2003/0037614 A1 * | 2/2003 | Nguyen et al. ........... | 73/504.14 |
| 2004/0016287 A1 * | 1/2004 | Fu ............................ | 73/23.34 |
| 2004/0053434 A1 * | 3/2004 | Bruner ...................... | 438/52 |
| 2005/0003560 A1 * | 1/2005 | Zeng et al. ................ | 436/527 |
| 2005/0160816 A1 * | 7/2005 | Yu ............................ | 73/514.29 |
| 2006/0154248 A1 * | 7/2006 | McGrew et al. .......... | 435/6 |
| 2006/0223171 A1 * | 10/2006 | Craighead et al. ........ | 435/287.2 |
| 2008/0011053 A1 * | 1/2008 | Fleischer et al. .......... | 73/23.31 |

OTHER PUBLICATIONS

J.R. Vig., R.L. Filler, and Y. Kim. Chemical Sensor Based on Quartz Microresonators. Journal of Microelectromechanical Systems. 1996. 5(2): p. 138-140.

T. Thundat, G.Y. Chen, R.J. Warmack, D.P. Allison, and E.A. Wachter. Vapor Detection Using Resonating Microcantilevers. Anaytical Chemistry. 1995. 67(3): p. 519-521.

(Continued)

*Primary Examiner*—David A. Rogers
(74) *Attorney, Agent, or Firm*—Harness, Dickey & Pierce, P.L.C.

(57) ABSTRACT

A sensor is provided which is configured to detect the presence of multiple analytes, for example chemical or biological compounds, through the measurement of induced resonance shifts in a coupled array of microelectromechanical or micromechanical resonators.

21 Claims, 20 Drawing Sheets

OTHER PUBLICATIONS

T. Thundat, P.I. Oden, and R.J. Warmack. Microcantilever Sensors. Microscale Thermophysical Engineering. 1997. 1(3): p. 185-199.

H.P. Lang, M. Hegner, and C. Gerber. Cantilever Array Sensors. Materials Today. 2005. 8(4): p. 30-36.

A. Alsuwaiyan and S.W. Shaw. Localization of Free Vibration Modes in Systems of Nearly-Identical Vibration Absorbers. Journal of Sound and Vibration. 1999. 228(3): p. 703-711.

K.L. Turner, P.G. Hartwell, and N.C. MacDonald. Multi-dimensional MEMS Motion Characterization Using Laser Vibrometry. In Proceedings of Transducers '99: The 10th International Conference on Solid-state Sensors and Actuators. 1999. Sendai, Japan.

B.E. DeMartini, J.F. Rhoads, S.W. Shaw, and K.L. Turner. A Single Input-Single Output Mass Sensor Based on a Coupled Array of Microresonators. Sensors and Actuators A 137 (2007): p. 147-156.

T. Thundat, E.A. Wachter, S.L. Sharp, and R.J. Warmack. Detection of Mercury Vapor Using Resonating Microcantilevers. Applied Physics Letters 66 (13), Mar. 27, 1995; p. 1695-1697.

B. Ilic, D. Czaplewski, H.G. Craighead, P. Nezil, C. Campagnolo, and C. Batt. Mechanical Resonant Immunospecific Biological Detector. Applied Physics Letters vol. 77, No. 3, Jul. 17, 2000: p. 450-452.

T. Ono, X Li, H. Miyashita, and M. Esashi. Mass Sensing of Adsorbed Molecules in Sub-Picogram Sample with Ultrathin Silicon Resonator. Review of Scientific Instruments vol. 74, No. 3, Mar. 2003: p. 1240-1243.

M. Su, S. Li, and V.P. Dravid. Microcantilever Resonance-Based DNA Detection with Nanoparticle Probes. Applied Physics Letters, vol. 82, No. 20, May 19, 2003: p. 3562-3564.

N. Nugaeva, K.Y. Gfeller, N. Backmann, H.P. Lang, M. Duggelin, and M. Hegner. Micromechanical Cantilever Array Sensors for Selective Fungal Immobilization and Fast Growth Detection. Biosensors and Bioelectronics 21 (2005): p. 849-856.

A. Zribi, A Knoblock, Wei-Cheng Tian, S. Goodwin. Micromachined Resonant Multiple Gas Sensor. Sensors and Actuators A 122 (2005): p. 31-38.

K.Y. Gfeller, N. Nugaeva, M. Hegner. Micromechanical Oscillators as Rapid Biosensor for the Detection of Active Growth of *Escherichia coli*. Biosensors and Bioelectronis 21 (2005): p. 528-533.

Y.T. Yang, C. Callegari, X.L. Feng, K.L. Ekinici, and M.L. Roukes. Zeptogram-Scale Nanomechanical Mass Sensing. NANO Letters, vol. 6, No. 4, Apr. 2006: p. 583-586.

N.V. Lavrik, M.J. Sepaniak, P.G. Datskos. Cantilever Transducers as a Platform for Chemical and Biological Sensors. Review of Scientific Instruments, vol. 75, No. 7, Jul. 2004: p. 2229-2253.

S. Dohn, R. Sandberg, W. Svendsen, and A. Boisen. Enhanced Functionality of Cantilever Based Mass Sensors Using Higher Modes. Applied Physics Letters 86, 233501 (2005) 3 pgs.

M. Spletzer, A. Raman, A.Q. Wu, X. Xu, and R. Reifenberger. Ultrasensitive Mass Sensing Using Mode Localization in Coupled Microcantilevers. Applied Physics Letters 88, 254102 (2006): 3 pgs.

A Qazi, D. Nonis, A. Pozzato, M. Tormen, M. Lazzarino, S. Carrato, and G. Scoles. Asymmetrical Twin Cantilevers for Single Molecule Detection. Applied Physics Letters 90 17338 (2007): 3 pgs.

M.K. Baller, H.P. Lang, J. Fritz, Ch. Gerber, J.K. Gimzewski, U. Drechsler, H. Rothuizen, M. Despont, P. Vettiger, F.M. Battiston, J.P. Ramseyer, P. Fornaro, E. Meyer, and H.J. Guntherodt. Ultramicroscopy 82 (2000): 9 pgs.

\* cited by examiner

TABLE 1

| PARAMETER | DESCRIPTION |
|---|---|
| $\tau = \omega_0 t$ | NONDIMENSIONAL TIME |
| $\Omega = \dfrac{2\omega}{\omega_0}$ | NONDIMENSIONAL EXCITATION FREQUENCY |
| $(\bullet)' = \dfrac{d(\bullet)}{d\tau}$ | NEW DERIVATIVE OPERATOR |
| $u = \dfrac{\hat{x}}{x_0}, \quad v_i = \dfrac{\hat{z}_i}{x_0}$ | NONDIMENSIONAL DISPLACEMENTS |
| $\hat{m}_i = \dfrac{\hat{m}_i}{M}$ | INERTIA RATIO |
| $\Lambda = \dfrac{\omega_b}{\omega_0} = \dfrac{1}{\omega_0}\sqrt{\dfrac{k_b}{M}}$ | FREQUENCY RATIO |
| $\Upsilon_i = \dfrac{\omega_i}{\omega_0} = \dfrac{1}{\omega_0}\sqrt{\dfrac{k_i}{m_i}}$ | FREQUENCY RATIO |
| $\zeta_b = \dfrac{c_b}{2\sqrt{k_b M}}$ | DAMPING RATIO |
| $\zeta_i = \dfrac{c_i}{2\sqrt{k_i m_i}}$ | DAMPING RATION |
| $\zeta_{bi} = \dfrac{c_{bi}}{2\sqrt{k_i m_i}}$ | PSEUDO-DAMPING RATIO |
| $\Gamma = \dfrac{F_0}{M x_0 \omega_0^2}$ | NONDIMENSIONAL EXCITATION AMPLITUDE |

SENSOR WITH MICROELECTRO-MECHANICAL OSCILLATORS

CROSS-REFERENCE TO RELATED APPLICATIONS

This application claims the benefit of U.S. Provisional Application No. 60/810,783, filed on Jun. 2, 2006. The disclosure of the above application is incorporated herein by reference.

FIELD

The present disclosure relates to an analyte sensors and, more particularly, to a multi-analyte sensor which uses microelectro-mechanical oscillators to detect the presence individual analyte.

BACKGROUND

The statements in this section merely provide background information related to the present disclosure and may not constitute prior art.

Chemical and biological sensors based on microresonantors have been considered viable alternatives to modern sensing systems for some time, undoubtedly because they consume less power and space than their macroscale counterparts. Traditionally, these systems track resonance shifts in single-degree-of-freedom oscillators induced by mass or stiffness changes. As these changes are caused by local bonding, stress stiffening, or a similar chemical-mechanical process, the resonance shifts, in turn, indicate the presence of a given analyte. Existing sensors require the measurement of the response of an individual resonator for the detection of a specific compound, or a class of compounds. Large sensor arrays composed of isolated microresonators can be used to broaden detection capabilities, but the addition of the attendant electronics (arising from a larger number of system outputs) adds to the complexity of such sensor systems.

Existing methods of resonant microscale sensing detect a single target analyte by measuring induced resonance shifts in a single, isolated microresonator, which features independent actuation and sensing mechanisms. Multiple analytes can be detected with arrays of microresonators that have either collective or independent actuation; however, current techniques require independent sensing mechanisms for each resonator or a single sensing mechanism which operates in a scanning mode to recursively measure the response of each individual resonator. The first approach limits the number of analytes that can be detected and the second yields a relatively complex system with multiple inputs and outputs.

SUMMARY

It is an object of the present invention to overcome the disadvantages of the prior art. As such, a sensor is provided which is configured to detect the presence of multiple analytes (e.g., chemical or biological compounds) through the measurement of induced resonance shifts in a coupled array of microelectromechanical or micromechanical resonantors.

In one embodiment, an analyte sensor is provided having a sensing element with at least two vibrating members, each with a respective first resonant frequency, wherein the vibrating members are configured to detect the presence of a plurality of analytes. The analyte sensor further has a drive element coupled to the sensing element, the drive element being configured to apply force to the sensing element to induce a vibration within the sensing element. A vibration sensor is configured to measure changes of a resonant frequency of at least one of the vibrating members.

In another embodiment, an analyte sensor is provided having first and second masses vibrationally coupled to a shuttle mass. The first mass has a first resonant frequency in the absence of a first analyte, and a second resonant frequency after the exposure to the first analyte. The second mass has a third resonant frequency in the absence of a second analyte, and a fourth resonant frequency after the exposure to the second analyte. The analyte sensor further has a vibration sensor configured to detect vibration of the shuttle mass.

In another embodiment, a material detection sensor is provided having a base mass and first and second beams vibrationally coupled to the base mass. The first beam having a first resonant frequency in the absence of a first analyte, and a second resonant frequency after the exposure to the first analyte; the second beam having a third resonant frequency in the absence of a second analyte, and a fourth resonant frequency after the exposure to the second analyte. A vibration sensor configured to detect vibration of the base mass. An actuator configured to drive the shuttle mass.

In yet another embodiment, a sensor is provided having a support mass vibrationally coupled to a base. First and second cantilevered beams vibrationally are coupled to the support mass, with the first beam having a first resonant frequency in the absence of a first analyte, and a second resonant frequency in the presense the first analyte. The second beam having a third resonant frequency in the absence of a second analyte, and a fourth resonant frequency in the presence of the second analyte. A vibration sensor is further provided which is configured to detect vibration of the shuttle mass. An actuator provided to drive the shuttle mass at a series of predetermined frequencies.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 1A:
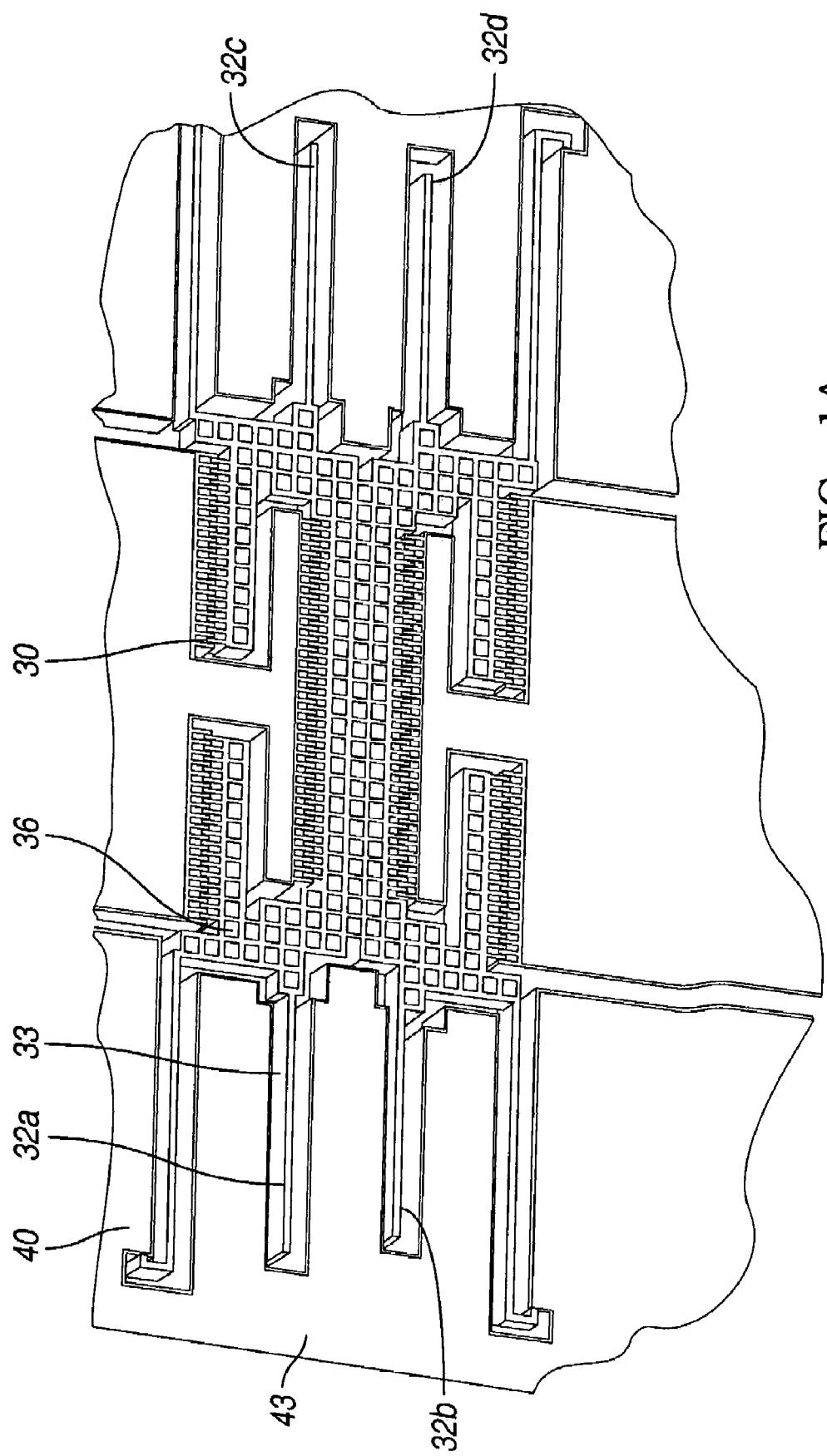
FIGS. 1A-1D represents a micrograph of a translational, SISO, multi-analyte sensor according to the present teachings.
Figure 1B:
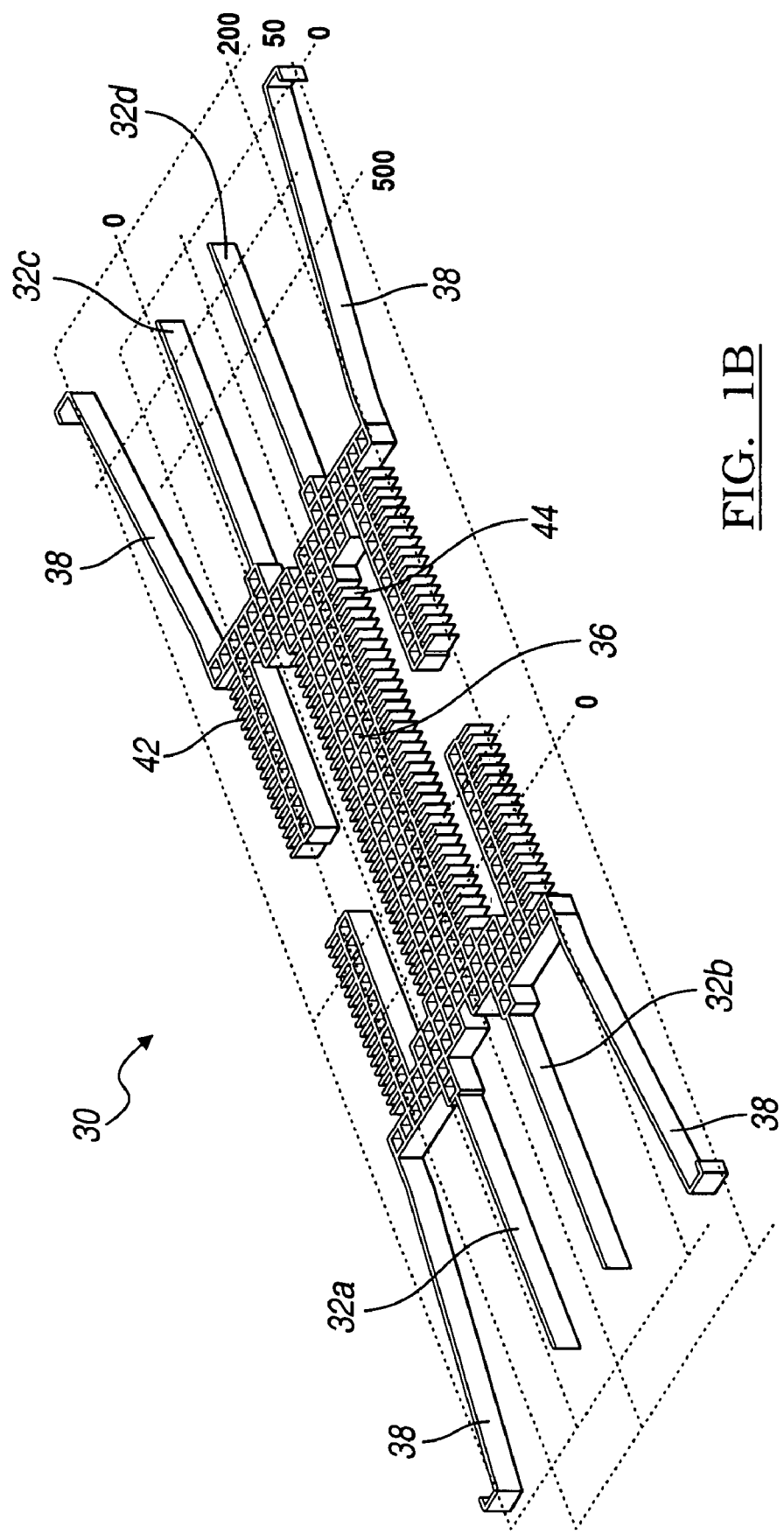
Figure 1C:
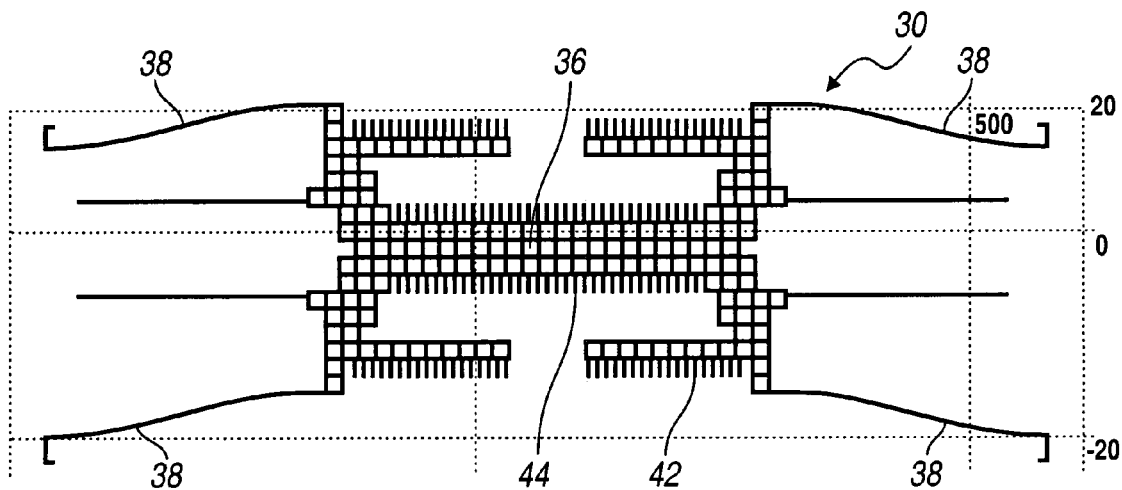

Table 1 represents non-dimensional parameter definitions.

DETAILED DESCRIPTION

The following description is merely exemplary in nature and is not intended to limit the present disclosure, application, or uses.

FIG. 1 represents a single input-single output sensor 30 which is configured to detect the presence of multiple analytes (e.g., chemical or biological compounds) through the measurement of induced resonance shifts in a coupled array of microelectromechanical or micromechanical resonators.

The sensor 30 exhibits the ability to detect multiple analytes with only a single input and a single output (SISO), that is a single excitation signal is all that is required to drive the device and a single output signal contains all of the information necessary for multiple analyte detection (and potentially identification). The sensor 30 exploits induced resonance shifts in a coupled microresonator array 33. The sensor has a number of secondary (frequency mistuned) resonators 32 coupled to a primary microresonator or shuttle mass 36. This primary resonator mass 36 is used for both actuation and sensing purposes. Induced resonance shifts in each of these secondary resonators 34 are detectable through the response of the primary resonator mass 36. This allows for rapid detection, and potentially the identification, of a variety of analytes on a single sensor platform in an efficient (SISO) manner.

While the examples herein are directed to the detection of gaseous chemicals, the system is equally usable for gaseous or liquid chemical or biological detection. It is envisioned these mass sensors 30 based on resonant microsystems are usable for (and, in some cases, implemented in) security, medical, research, and industrial applications. The sensor system is principally proposed for microscale development. As such, it can be constructed through any of a large number of microfabrication processes (i.e., standard silicon on insulator processing, SCREAM processing, etc. . . . ). Additionally details relating to such processes can be found in the literature (see, for example, Madou, 1997).

FIG. 1A depicts a resonant single input-single output (SISO) sensor 30 based on a coupled array of microelectromechanical or micromechanical oscillators 32 according to the teachings herein. The sensor 30 exploits resonance shifts induced by mass and/or stiffness changes, resulting from local bonding, stress stiffening, or a similar chemical-mechanical process, to indicate the presence of (and potentially identify) a particular analyte or group of analytes. The sensor 30 allows for detection of multiple analytes is accomplished using a single excitation signal and, more significantly, the measurement of a single output signal. This results in a resonant sensor 30 that maintains the inherent benefits of microscale sensor arrays, namely small size and high sensitivity, yet does so in the context of a simple system that requires significantly less attendant hardware and signal processing than other known alternatives.

With general reference to FIGS. 1A-1D, which represent a sensor 30 found within a silicon substrate 41, the sensor 30 has a plurality of mistuned masses or microbeams 32a-32d. These masses, 32a-32d, take the form of beams 33 coupled to the shuttle mass 36. The beams 32a-32d can be cantilevered or can be coupled at two ends to the shuttle mass 36. The shuttle mass 36 is vibrationally coupled to a base or ground 43 through at least one support member 38. Additionally associated within the sensor 30 are an actuator 42 and a system vibration sensor 44. The actuator 42 is configured to drive the shuttle mass at discrete frequencies between a first predetermined frequency and a second predetermined frequency.

Optionally, the mistuned masses 32a-32d can be configured to detect different materials. In this regard, the mistuned masses 32a-32d can be formed of or coated with differing materials which will absorb the analyte at different rates. In doing this, the presence of the first analyte will cause the resonant frequency of one beam to shift away from a first frequency to a second frequency. Additionally, in the presence of a second analyte, the resonant frequency of a second beam 32b can shift from a third resonant frequency to a fourth resonant frequency. It is envisioned that this frequency shift can be accomplished with a shift in the spring constant K, damping C, and/or addition of mass M to the mistuned masses 32a-32d. For example, in gas-detection situations, it has been found that the change in spring constant is the primary mechanism to shift the response of the system.

Figure 1D:
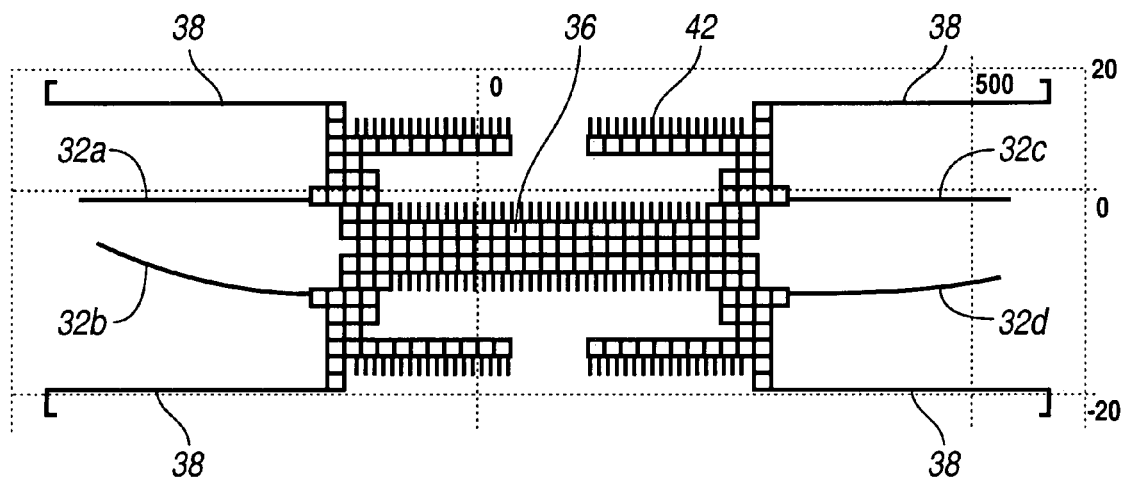
Figure 2A:
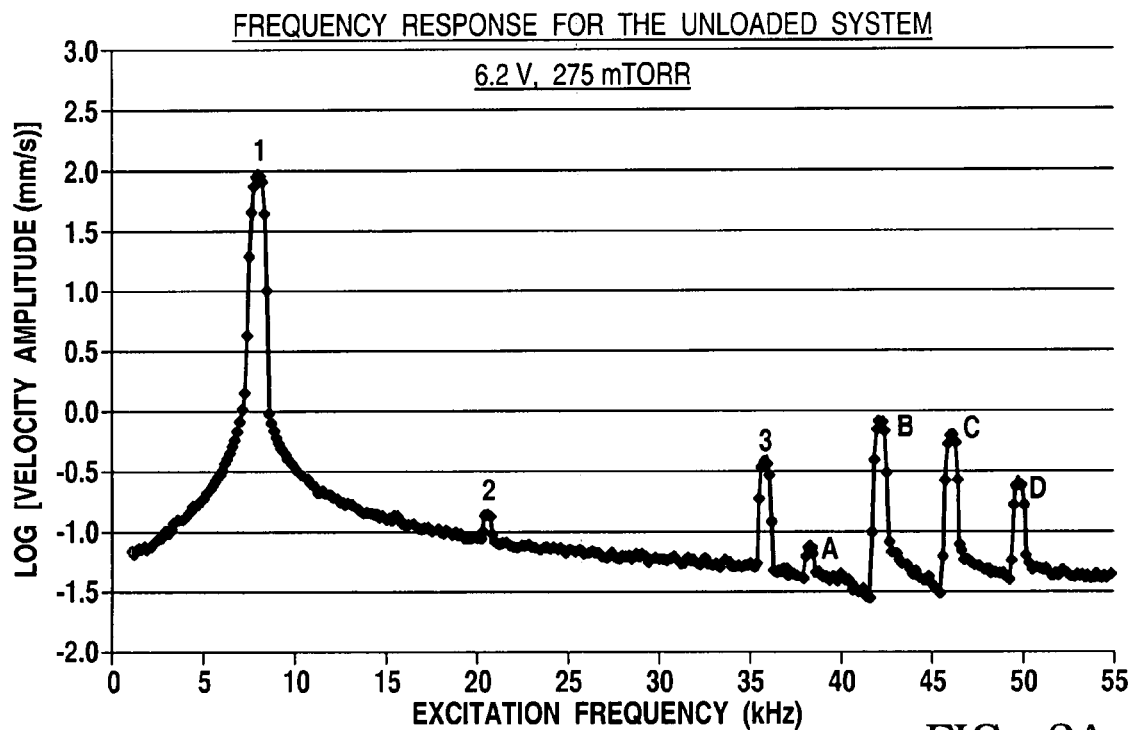
FIGS. 2A and 2B represent response curves of the sensor shown in FIG. 1.

FIG. 2A depicts a frequency response for the device shown in FIGS. 1A and 1D obtained experimentally using a laser vibrometer. As shown, the system exhibits a distinct low frequency resonance corresponding to a translational mode of the overall system (1), two resonances corresponding to out-of-plane modes (2,3), and four resonances corresponding to the localized modes of the microbeams 32a-32d (A,B,C,D), the latter of which have been verified with a stroboscopic in-plane measurement system and video images. Sweeping through a frequency range that covers the beam resonances allows for the detection of resonance shifts in each of the microbeams 32a-32d.

To effectuate the shift in resonant frequency in the microbeams 32a-32d, the detection beams 32 can be formed of or be coated with Silicon, Polycrystalline Silicon, Amorphous Silicon, Polycrystalline Diamond, Amorphous Diamond, Gallium Arsenide, Silicon Nitride, Silicon Carbide, Titanium, Gold, Aluminum, Aluminum Nitride, Nickel, Silicon Dioxide, Pyrex (glass), Chromium, Photoresist, Buffer solutions, Platinum, Titanium oxide, or combinations thereof. Additionally, the detection beams 32 can be formed of or be coated with PMMA and other polymer substances for gas sensing.

Figure 2B:
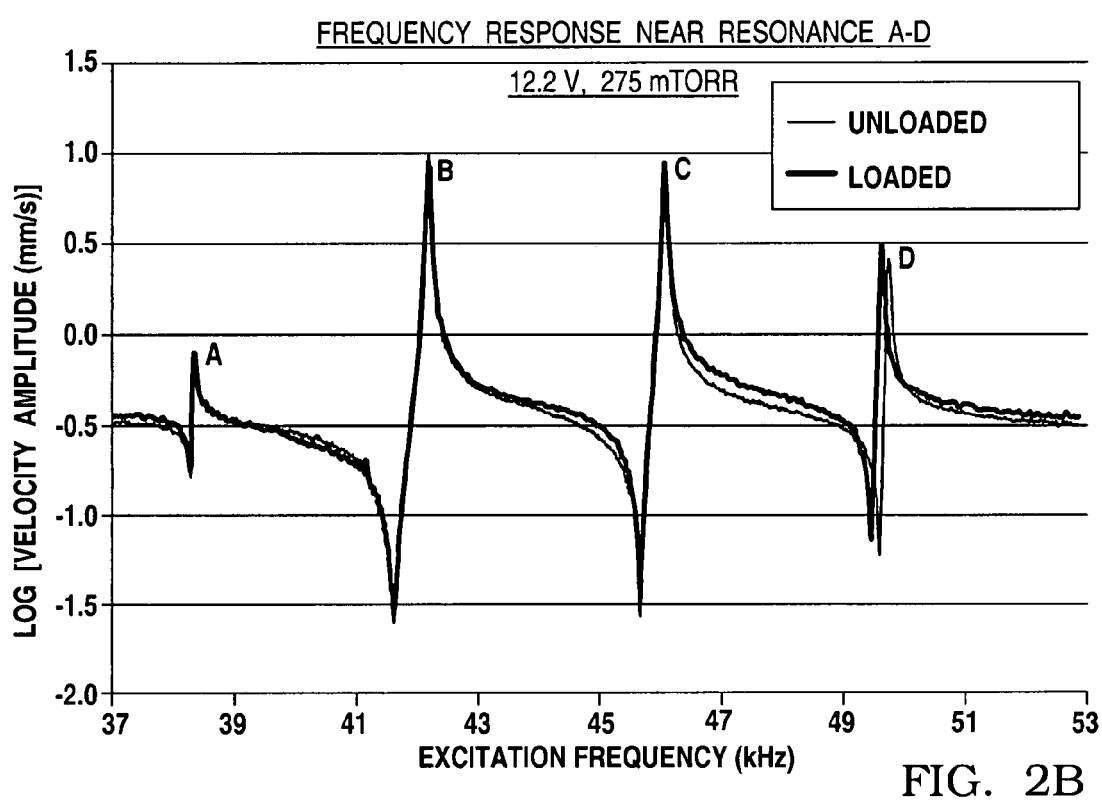

Mass detection was simulated by obtaining an initial frequency response for the shuttle mass 36 and comparing it to the frequency response of the shuttle mass 36 following the deposition of a small amount of platinum on the highest frequency microbeam. A focused ion beam was used to deposit a 1.57×5.10×0.22 μm patch of platinum, see FIG. 3, on the desired microbeam, yielding an approximate mass change of 38 pg. Note that this added mass changed all of the resonance peaks in this coupled set of beams, but that due to the localized nature of the response, the shift in the peak of interest (D) was about 50 times that of the other peaks (see FIGS. 2b and 4a,4b). Additionally, the sensor exhibited a mass resolution of approximately 3 Hz/pg, a value comparable to alternative sensor designs. It is envisioned absorbing material can be added to exterior surface of the microbeams 32a-32d.

Through a number of topologically equivalent geometries can be developed based on the sensing principles discussed herein, the translational design depicted in FIGS. 1A-1D was selected as an example. This relatively simple sensor geometry consists of the shuttle mass 36 that is suspended above the substrate by four folded beam flexures 38 and driven by interdigitated electrostatic comb drive actuator 42. Attached to this shuttle are four microbeam oscillators 32a-32d each with slight frequency mistuning, as realized through small length variations, to ensure ample separation of the coupled system's natural frequencies—a desirable precursor for localization, as subsequently described.

Figure 5:
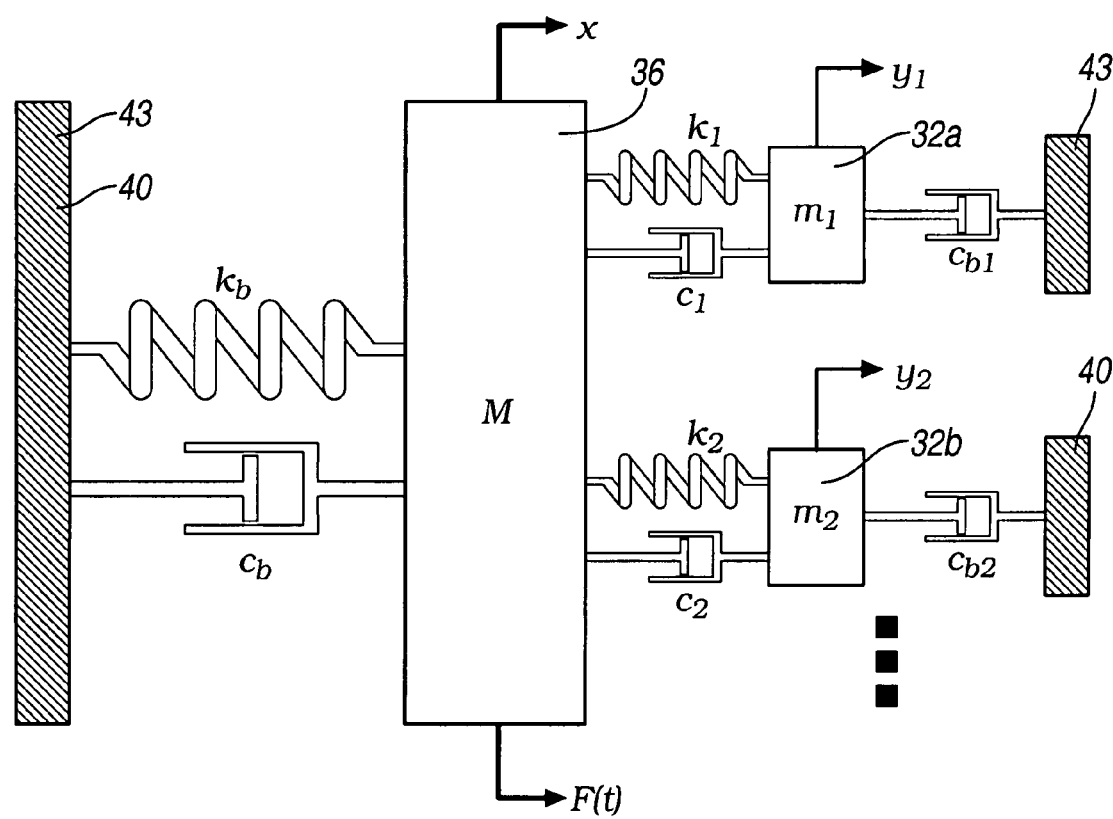
FIG. 5 represents a mass-spring-dashpot analog of the sensor shown in FIG. 1.

The relevant response characteristics of the device shown in FIGS. 1a-1d can be described through the use of the simple linear lumped-mass model shown in FIG. 5. Here the N microbeam oscillators are represented by the smaller masses, m1, m2, etc., and the comparatively larger shuttle mass 36 is represented by M. It is important to note that while topologies such as that shown in FIG. 5 are believed to be novel in the sensors community, they have garnered attention in other contexts, namely noise control and vibration suppression. Unfortunately, given the stark contract between these applications and that considered here, as well as the requisite form of each of the systems' frequency responses, the results of the previous works are not directly applicable to the present study.

The equations of motion governing the system depicted in FIG. 5 are given by $$M\ddot{x} + \sum_i m_i(\ddot{x} + \ddot{z}_i) + \sum_i c_{bi}(\dot{x} + \dot{z}_i) + c_b \dot{x} + k_b x + F(t),$$

where $z_i$ is the relative displacement of the ith subsystem, given by $$m_i(\ddot{x}+\ddot{z}_i)+c_{bi}(\dot{x}+\dot{z}_i)+c_i\dot{z}_i+k_i z_i+O, \; i=1,\ldots,N,$$

$C_b$, $c_i$, $c_{bi}$ represent linear damping coefficients arising from intrinsic and extrinsic dissipation, and F(t) represents the electrostatic force produced by the interdigited comb drives.

Assuming ample device thickness (approximately 10 μm or larger) and a harmonic voltage excitation of the form $$V(t)=V_A \cos \omega t, \quad (4)$$

the electrostatis force, F(t), can be approximated by $$F(t) = \frac{\varepsilon_0 n h V^2(t)}{g} \; F(t) = \frac{\varepsilon_0 n h V_A^2}{2g}(1+\cos 2\omega t) = F_0(1+\cos 2\omega t).$$

Where $\varepsilon_0$ represents the free space permittivity, n the number of comb fingers on the electrostatic comb drive, g the gap between adjacent comb fingers, and h the device thickness. Nondimensionalizing the resulting equations of motion and redefining the dynamic variables x and z by translation according to $$\hat{x} = x - \bar{x} = x - \frac{F_0}{k_b}, \; \hat{z}_i = z_i.$$

to eliminate the explicit DC forcing term (which is dependent on $V_A$) results in a new set of governing equations given by $$u'' + 2\zeta_b \Lambda u' + \Lambda^2 u = \Gamma \cos \Omega \tau - \sum_i \hat{m}_i(u'' + v_i'') - \quad (8)$$

$$\sum_i 2\zeta_{bi} \hat{\Upsilon}_i m_i(u' + v_i'), \hat{m}_i(u'' + v_i'') +$$

-continued $$2\zeta_i \Upsilon_i \hat{m}_i v_i' + \hat{m}_i \Upsilon_i^2 v_i$$

$$= -2\zeta_{bi} \Upsilon_i \hat{m}_i(u' + v_i') \; i=1,\ldots,N$$

with system parameters defined as in Tab. 1. For the sake of analysis, these equations can be compiled into a standard matrix form given by $$MX''+CX'+KX=\phi(\tau) \quad (9)$$

where X represents the compiled state vector, M the effective mass matrix (which incorporates inertial coupling terms), C the effective damping matrix (which incorporates dissipative coupling terms), K the effective stiffness matrix, and $\phi(r^1)$ the effective forcing vector, which is sparse except for the first element. From this matrix equation, the system's response can be easily determined through a variety of standard techniques.

Because of the large number of parameters (4N+4) present in Eq. 9, a number of qualitatively distinct frequency responses can be realized using the sensor topology detailed in FIG. 5. Unfortunately, most of these responses are poorly suited for sensing. Several features of this response are worth noting. First, the response includes a low-frequency resonance (1), which approximately occurs at the resonant frequency $$\Omega_0 \approx \frac{1}{\omega_0} \sqrt{\frac{k_b}{M + \sum_i^N m_i}}$$

corresponding to a bulk, in-plane mode where essentially all of the microbeams 32a-32d are moving together with the shuttle mass 36 as a lumped mass. Additionally, the response includes four comparatively higher frequency resonances: (A), (B), (C), and (D). These resonances occur at frequencies slightly greater than $\gamma_i$ and correspond to in-plane modes where the system's energy is largely localized in, or confined to, a single microbeam (as confirmed by noting the comparatively larger resonant amplitudes). As these higher frequency resonances (corresponding to the localized modes) induce a measurable resonance in the response of the shuttle mass 36 M, resonance shifts induced by chemomechanical processes on any of the microbeams 32a-32d can be detected using solely the shuttle mass' response. Accordingly, sweeping the excitation frequency of the system Ω through a frequency domain that includes $\gamma_1,\ldots,\gamma_N$ allows for the detection of up to N distinct analytes, providing proper functionalization.

Figure 6:
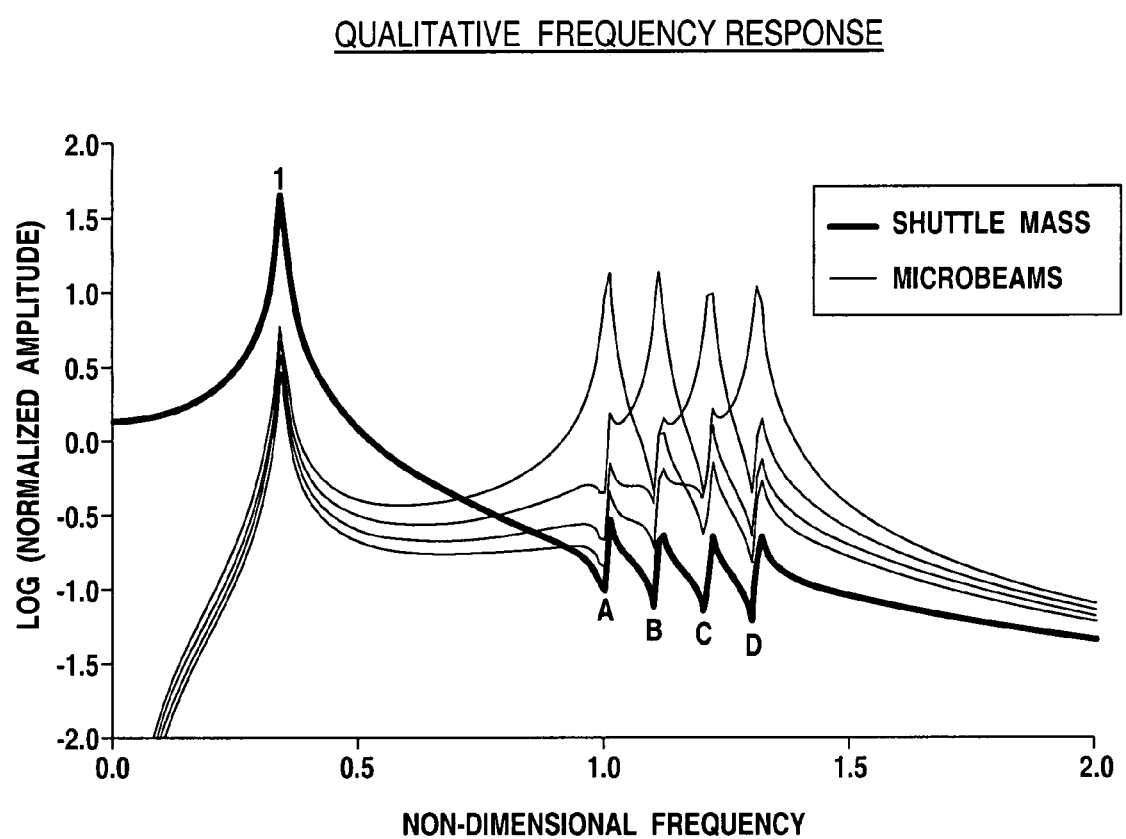
FIG. 6 represents a desirable form of the frequency response for a representative sensor design.

Given the large number of qualitatively distinct frequency responses that can be obtained for the system depicted in FIG. 5, it is important to note how responses similar to that shown in FIG. 6, which are well suited for resonant mass sensing, can be recovered through careful selection of system parameters. To this end, details on the selection of system inertia ratios ($m_i$), system frequency ratios ($\gamma_i/\Lambda$), and the amplitude of the AC voltage excitation applied to the electrostatic comb drives ($V_A$), which manifests itself in Γ, are detailed here.

To ensure ample separation between resonances (A), (B), (C), and (D), as well as all other resonances corresponding to both in-plane and out-of-plane modes, the frequency ratios ($\gamma_i/\Lambda$) must be carefully selected. Specifying ($\gamma_i/\Lambda$) too close to unity leads to little or no separation between the low-frequency resonance (1) and resonances (A)-(D). This results in the saturation of the resonant peaks associated with the localized modes, which can hinder the detection of resonance shifts, especially in the presence of additive noise. Similar decreases in resonant amplitudes can occur if the resonances occurring at approximately $\gamma_i$ are placed too close to resonances corresponding to out-of-plane modes or higher frequency in-plane modes (neither of which are captured with the lumped-mass model detailed here, but both of which could be captured through modal analysis of the structure using finite element techniques). It should also be noted that each ($\gamma_i/\Lambda$) value must be well separated from all other ($\gamma_i/\Lambda$) values, as placing two resonances too close together can lead to the formation of multi-resonance passband (i.e., the resonance peaks become indistinct), which prevents the detection of individual resonance shifts—a necessary for the SISO mass sensing methods detailed here.

Due to the presence of inertial coupling in Eq. 9, specification of the system's inertia ratios ($m_i$) is used to control the coupling strength between the microbeams 32a-32d and the shuttle mass 36, and thus is used in conjunction with frequency ratio selection to manipulate the degree of localization in the coupled system's response. For the device considered herein, strong mode localization is a prerequisite for efficient mass sensing. This can be attributed to the fact that while mass and/or stiffness changes in a single microbeam lead to shifts in all of the system's resonances, in the presence of strong mode localization these mass and/or stiffness changes induce a significantly larger shift in the resonance associated with the altered oscillator. This, providing selective surface functionalization, allows for the rapid identification of a given resonance shift's source (namely, the particular microbeam, which having undergone a chemomechanical process, has had its mass and/or stiffness altered), which may ultimately facilitate automated analyte identification.

Given the linear nature of the system detailed herein, manipulation of the AC excitation voltage amplitude ($V_A$) is used primarily to control the relative amplitude of the shuttle mass' response. As the ability to operate in low Q environments is an ultimate goal with this sensor, large amplitude responses, realized using a comparatively large excitation amplitude, are generally desirable. These large amplitudes, however, an lead to a nonlinear resonance structure, which proves problematic for sensing. As such, practical magnitude constraints on $V_A$ must be adopted and accounted for in the course of design.

To validate the SISO, multi-analyte sensor concept detailed herein, the device depicted in FIGS. 1a-1d was fabricated using a standard silicono-on-insulator (SOI) process flow, which included a single lithographic step, followed by a silicon deep etch (performed using DRIE), an $O_2$ reactive ion etch (RIE) to remove excess polymers, and, finally, a wet hydrofluoric acid (HF) etch to undercut and release the device. Mass detection was then simulated by comparing the sensor shuttle mass' frequency response before and after the deposition of a small amount of mass on the highest frequency microbeam resonator. Actuation can be provided electrostatically through the integrated comb drives and response measurements were obtained optically through single beam laser vibrometry. Note that as the device vibrates in-plane in the desired mode of operation, a 45° mirror was cut into the silicon adjacent to the shuttle mass 36 using a focused ion beam. This permitted the laser to be reflected off the mirror and onto the shuttle mass 36 itself, thus allowing for the direct acquisition of the shuttle mass' velocity.

Figure 7:
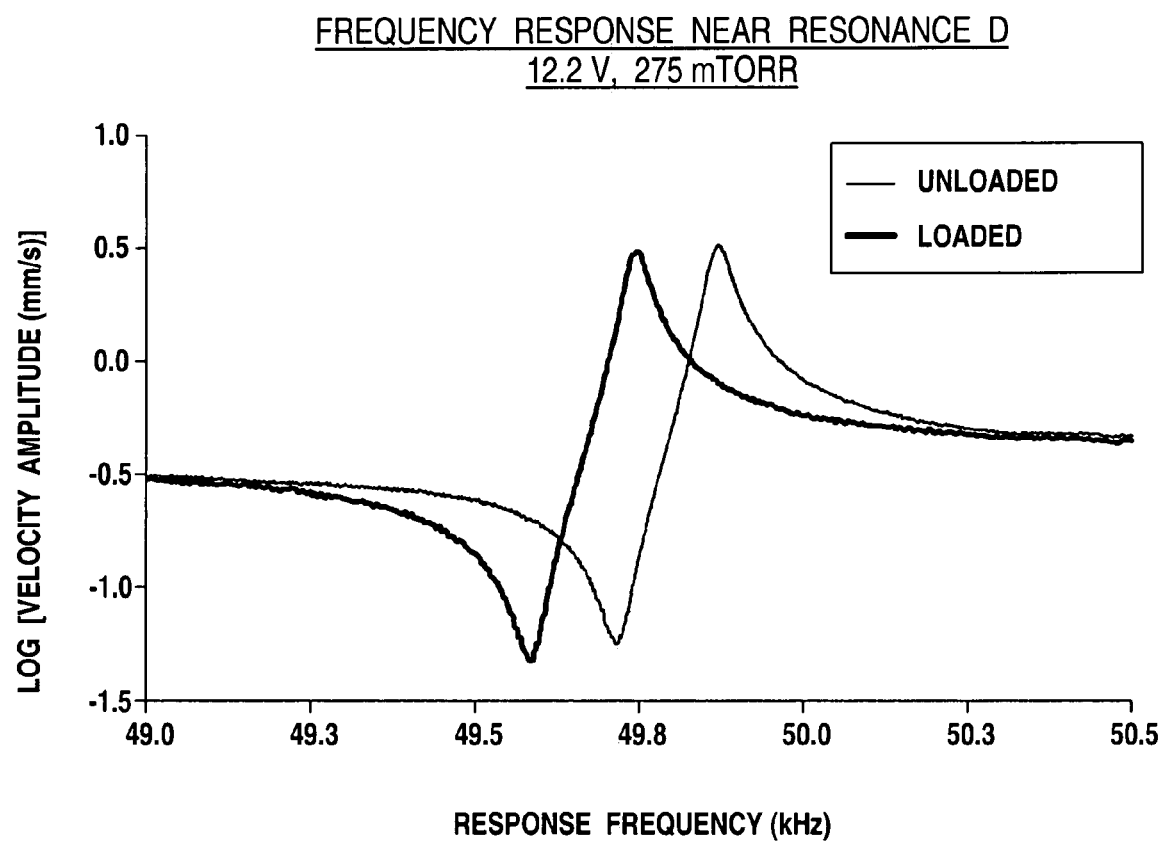
FIG. 7 represents an experimentally-obtained frequency response near resonance of the sensor depicted in FIG. 1.

FIG. 7 shows the frequency response acquired for the sensors depicted in FIGS. 1a-1d, actuated with a 6.2 V AC signal in 275 mTorr pressure, prior to added mass deposition. As evident, the response is largely compatible with the desired form of the frequency response shown in FIG. 6. Specifically, the response includes a low frequency resonance 91) at approximately 10 kHz, which corresponds to the bulk in-plane mode; two resonances (2) and (3), not predicted by the lumped-mass model, but subsequently predicted via finite element methods, at approximately 49 kHz and 63 kHz with approximately 5 kHz spacing, which correspond to the microbeam-localized modes of the system. It should be noted that the localized nature of the latter modes has been verified visually through the use of a stroboscopic in-plane measurement system with video capture capabilities.

Figure 3:
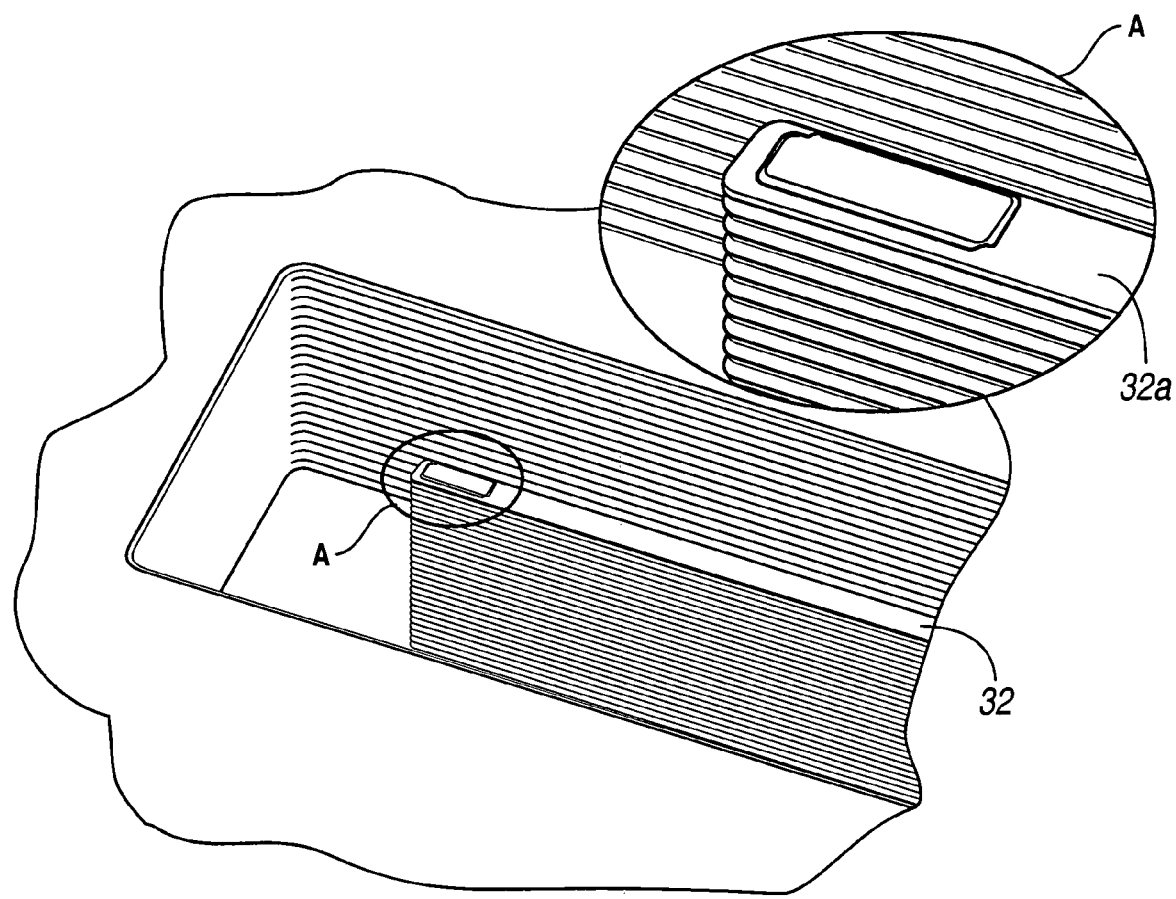
FIG. 3 represents an image of a platinum patch added to the sensor shown in FIG. 1.
Figure 4A:
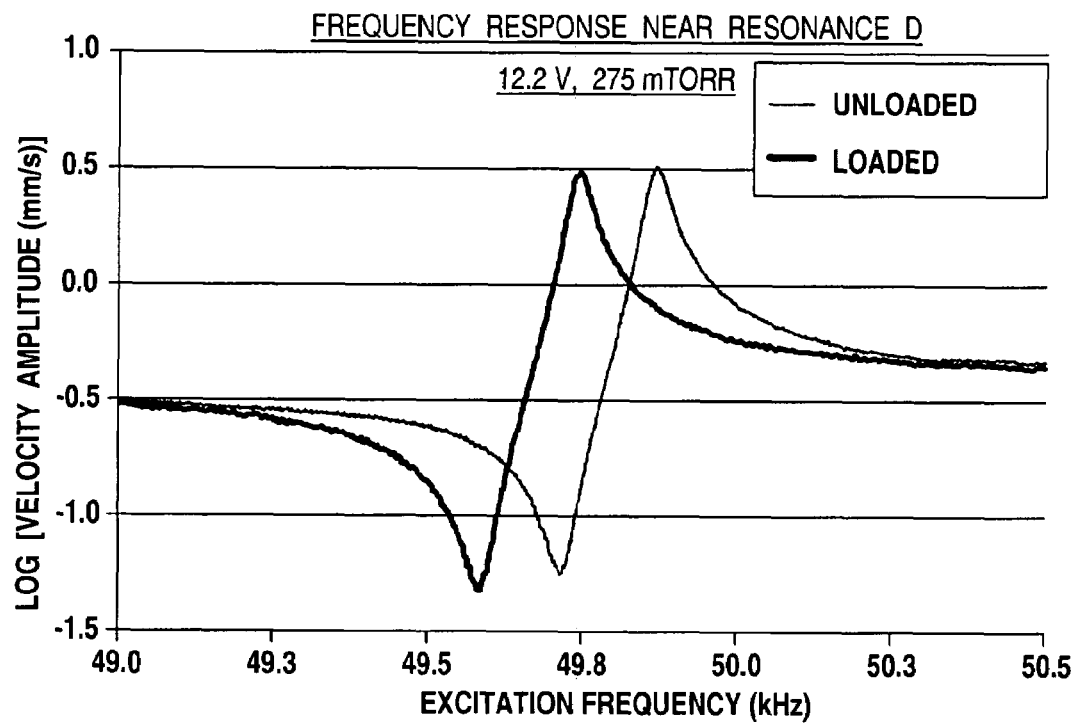
FIGS. 4A and 4B represent experimentally-obtained frequency response associated with the sensor shown on FIG. 1.
Figure 4B:
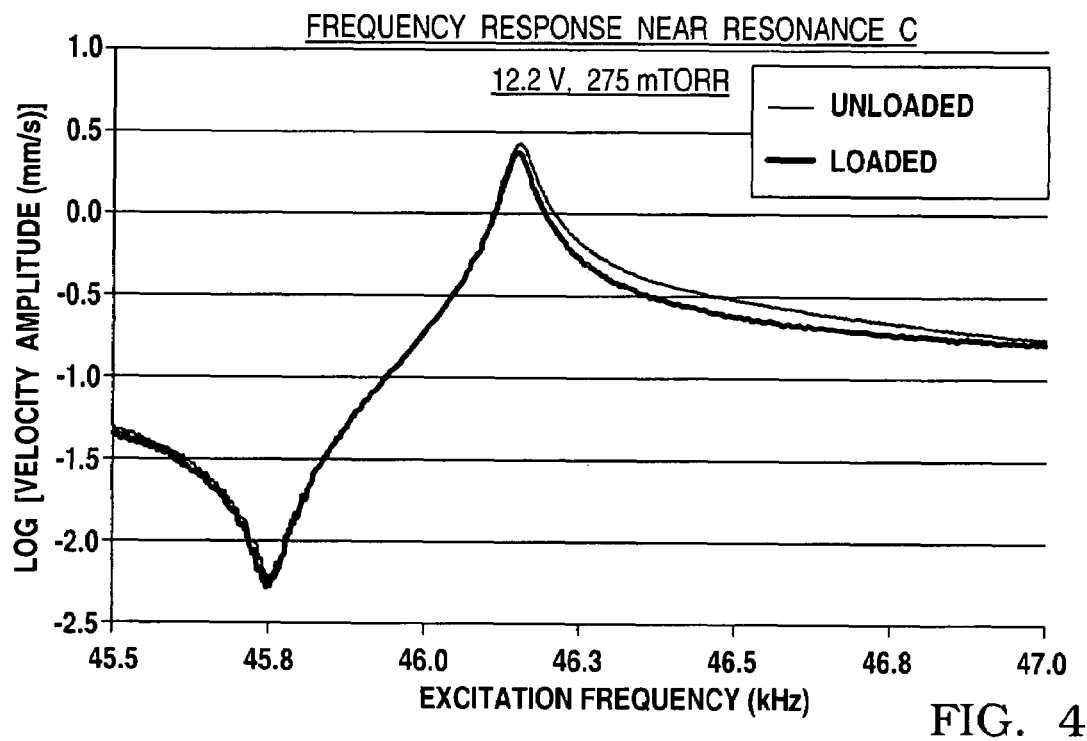
Figure 8:
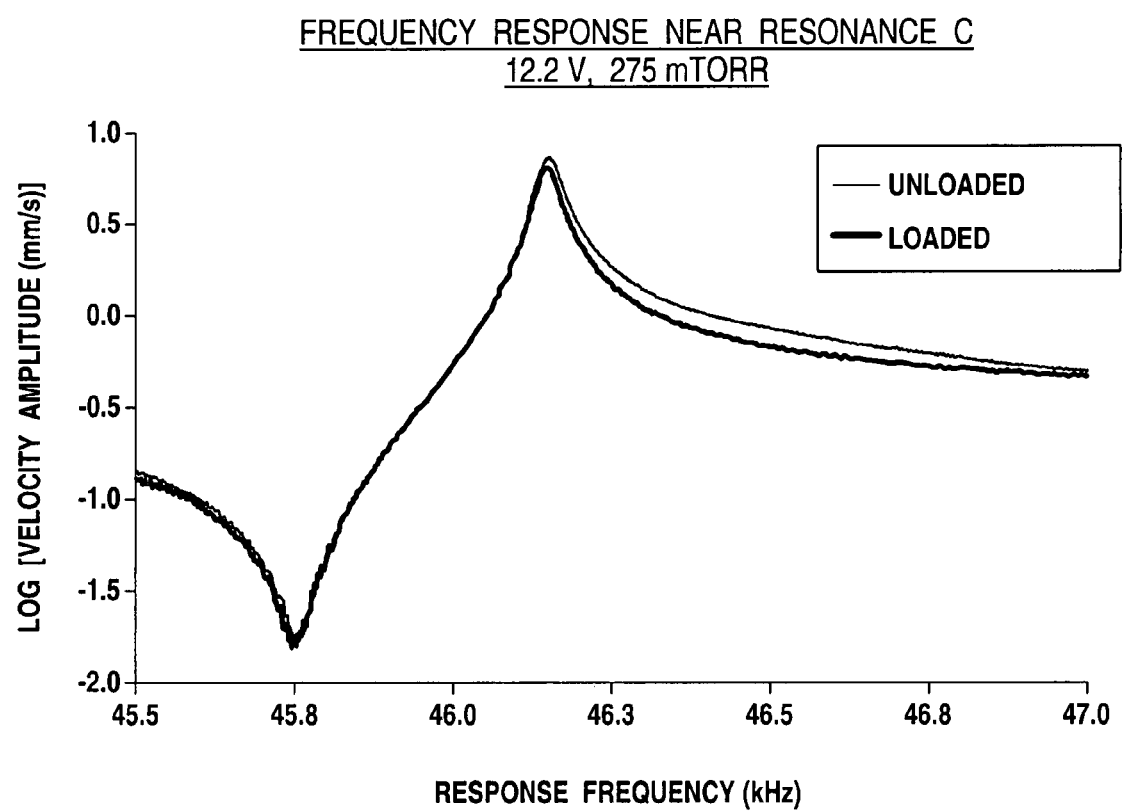
FIG. 8 represents a frequency response of near resonance for the sensor depicted in FIG. 1.

Following the acquisition of the frequency response data summarized in FIG. 7, a small platinum patch, measuring approximately 1.57×5.10×0.22 µm with an approximate mass of 38 pg, was deposited at the tip of the highest frequency microbeam using a focused ion beam (FIB) deposition system (see FIG. 3). The effect of this added mass is detailed in FIG. 8, which shows a close-up view of the sensor's frequency response near the four resonances corresponding to the localized microbeam modes, obtained prior to and after platinum deposition. As evident, the added mass caused shifts in each of the system's resonances, but the most pronounced shift, by far, occurred in the resonance associated with the localized mode of the highest frequency microbeam (that to which the platinum patch was added). This is verified through closer examination of the individual resonance peaks shown in FIG. 2B. Specifically, it is seen that resonance (D), that associated with the localized mode of the altered microbeam 32a, shifted by approximately 124 Hz and resonance (C), the resonance with the next largest shift, shifted by only approximately 3 Hz. Accordingly, due the localized nature of the sensor's response, the resonance shift associated with the mass added beam was approximately 40 times greater than that of the next largest resonance shift, a fact that could be used in implementation to identify the altered microbeam.

Figure 9:
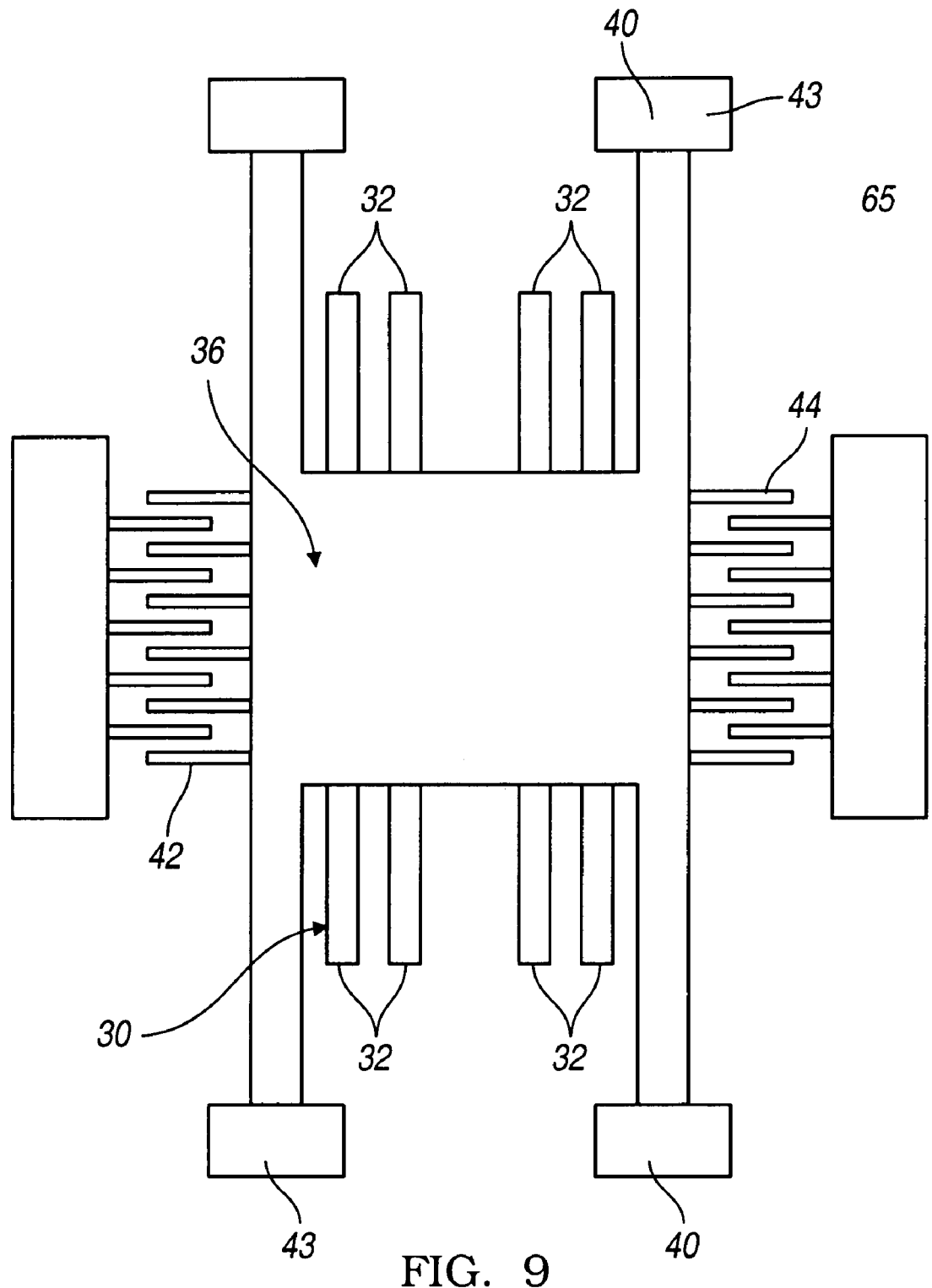
FIG. 9 represents another embodiment configured to detect small amounts of a single analyte.

FIG. 9 represents an alternate sensor 65 according to an alternate embodiment. The sensor 65 of the shuttle pass 36 coupled to ground using two pairs of supports beams 38. Disposed on the shuttle mass 36 is a plurality of cantilevered sensing beams 32. These beams 32 can have mismatched resonant frequencies or can have identical resonant frequencies. In this regard, the beams 32 having the same or similar resonant frequency can be configured to detect very small amounts of the same analytes. Additionally, it is envisioned that each of the sensing beams 32 can be mistuned masses, as described above, configured to detect varying analytes. Additionally shown are detecting and actuating combs 42 and 44.

Figure 10:
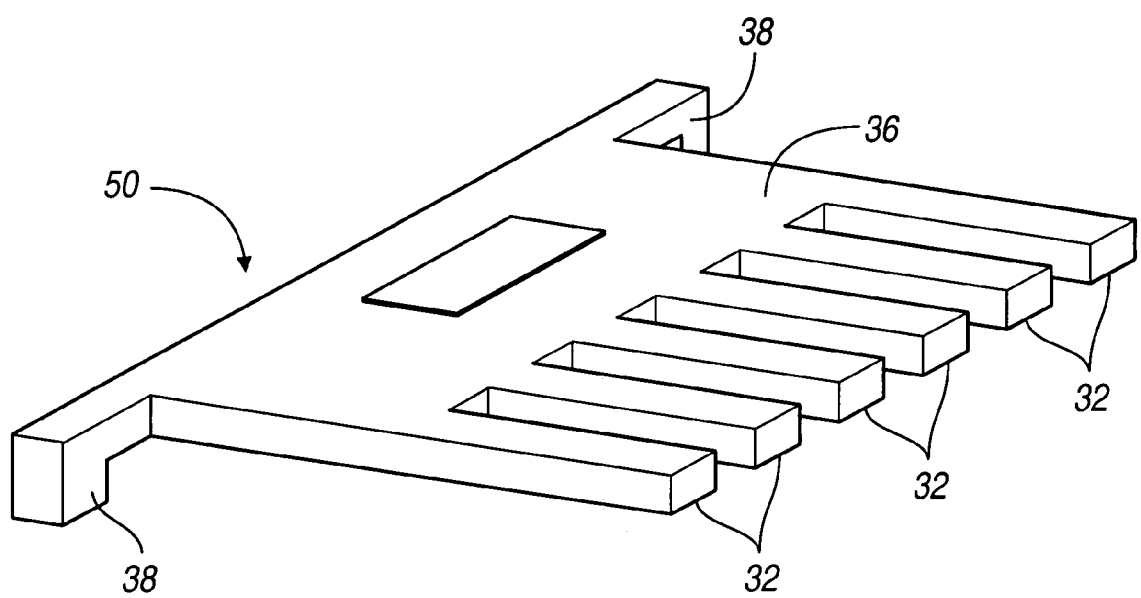
FIGS. 10-12 represent alternate sensor configurations.

FIG. 10 detects an alternate sensor configuration. Shown is the sensor 50 coupled to ground through at coupling members 38. The sensor 50 is formed of a suspended mass 36 and a plurality of dependent mistuned detection members 32. Optionally, the suspended mass 36 can be driven using a capacitor or electromagnetic drive. Additionally, the sensor 50 can have associated piezo detection sensor coupled to the shuttle mass 36.

Figure 11:
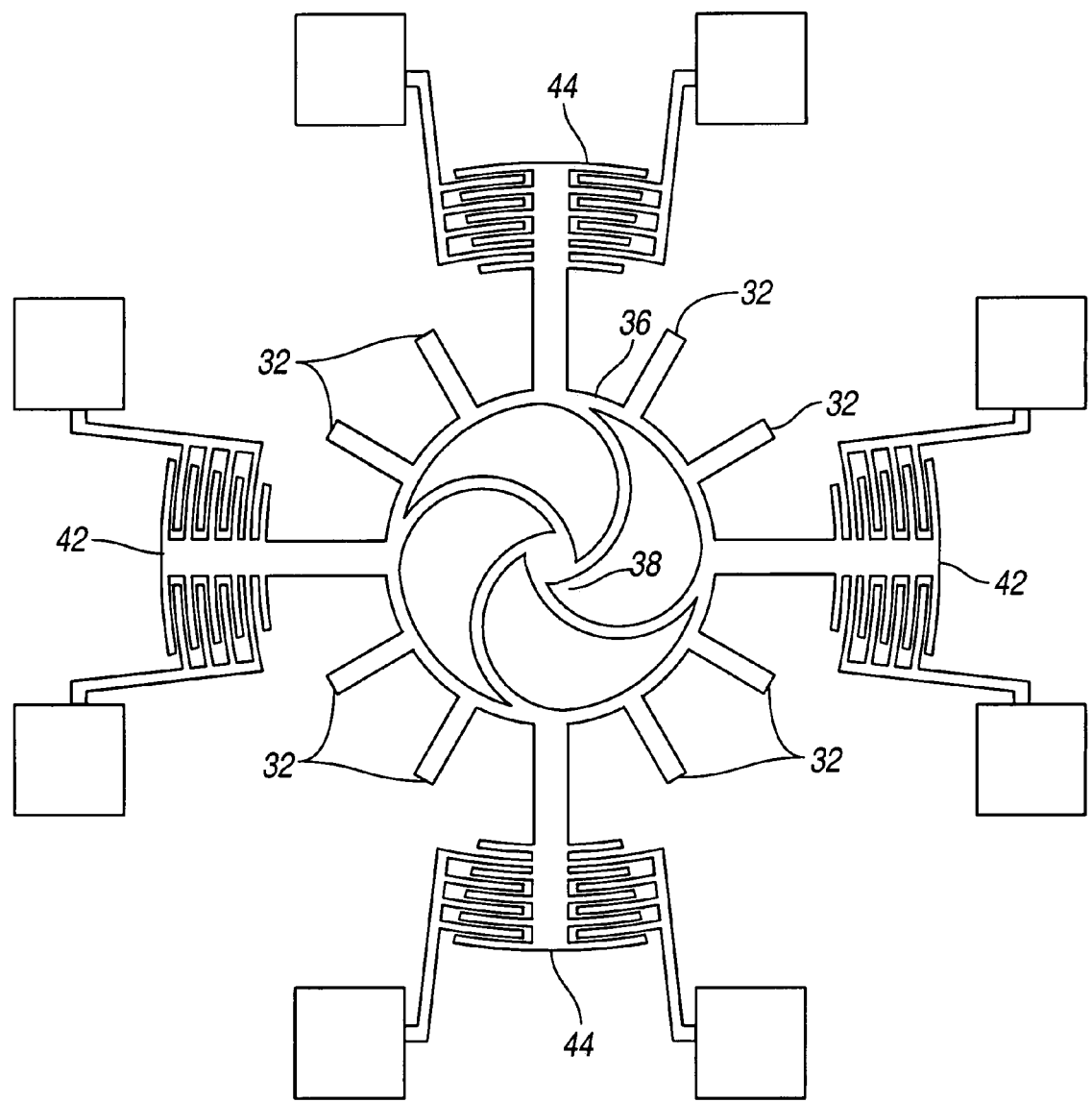
Figure 12:
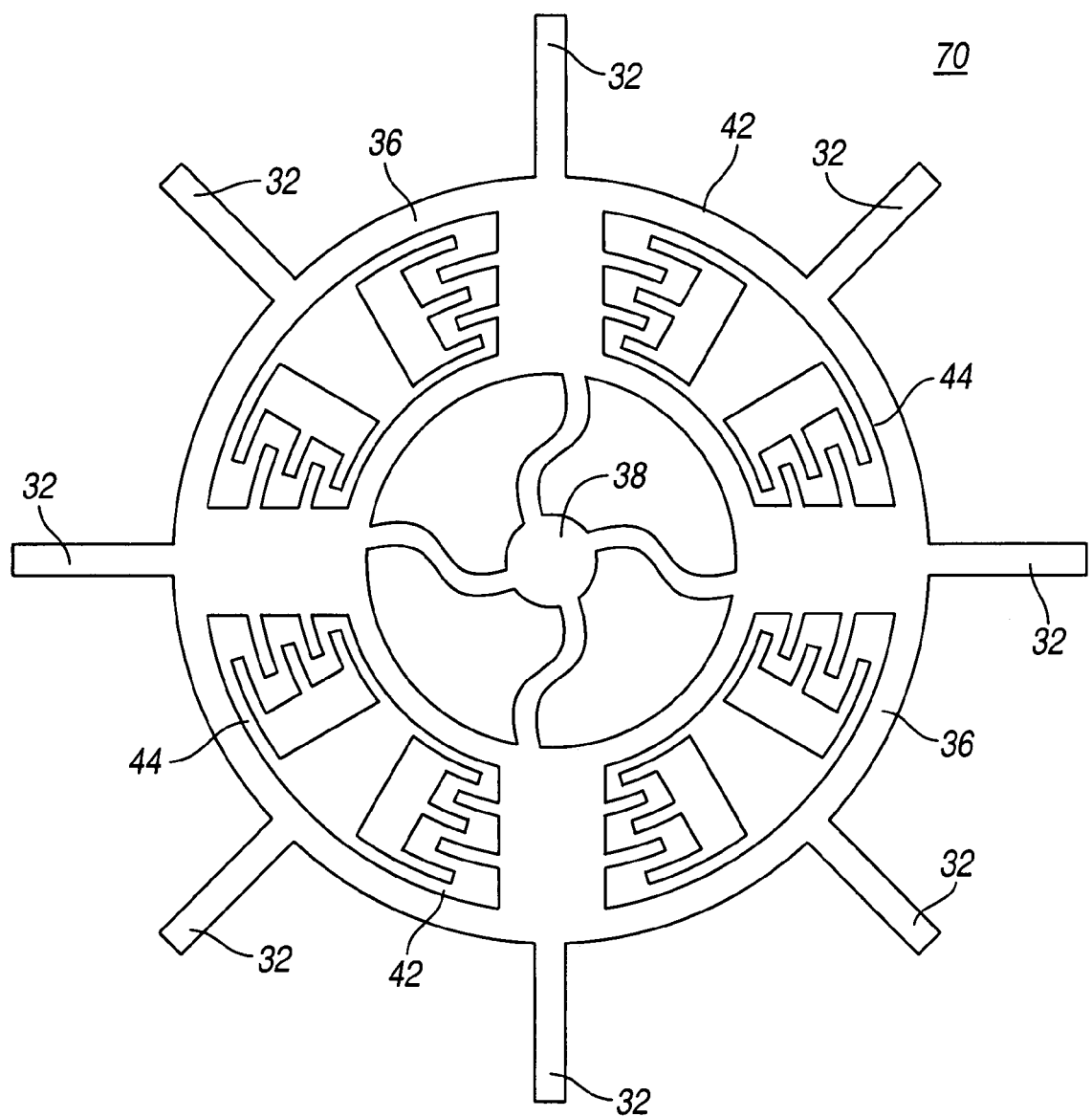

FIGS. 11 and 12 represent sensor 60 and 70 which are rotationally coupled to a base 50 using a central coupling member 38. The sensors 60 and 70 are configured to be driven by either internal or external drive combs 40. The drive combs 40 are coupled to a circular mass 36, which has a plurality of mistuned masses 32 that are radially disposed either inside or outside of the circular mass 36. As described above, the mistuned masses 32 are configured to individually detect disparate analytes.

Figure 13:
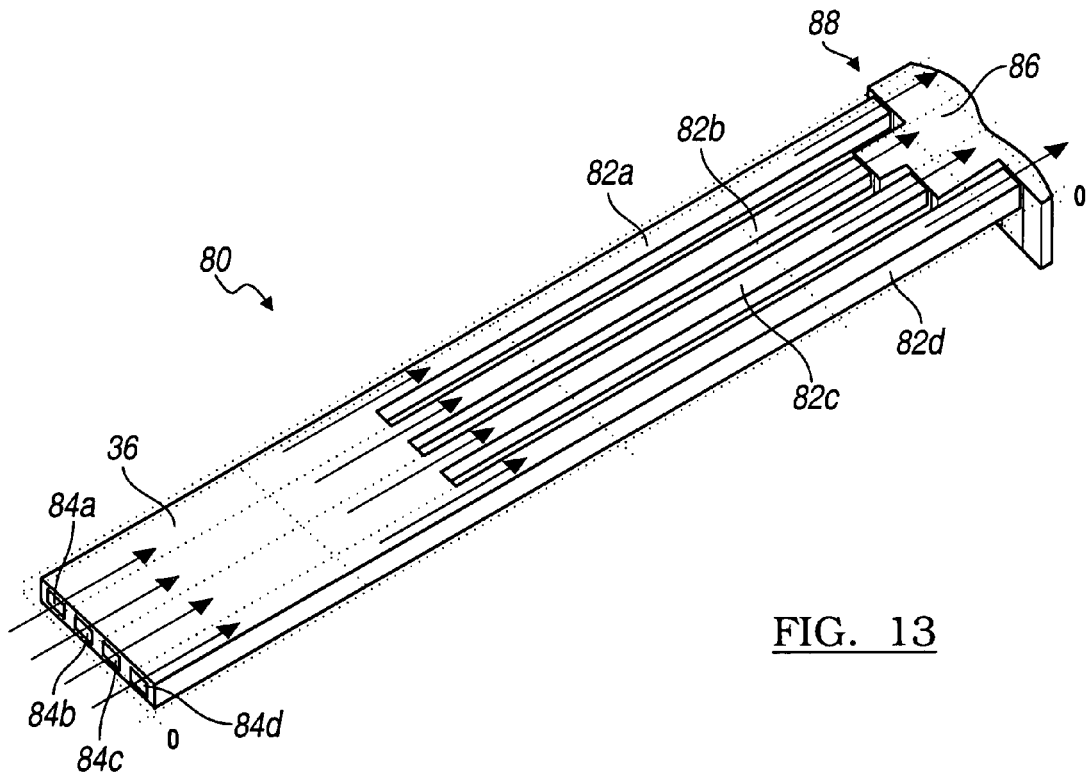
FIG. 13 represents an alternate sensor configured to detect the presence of a material in a fluid.
Figure 14A:
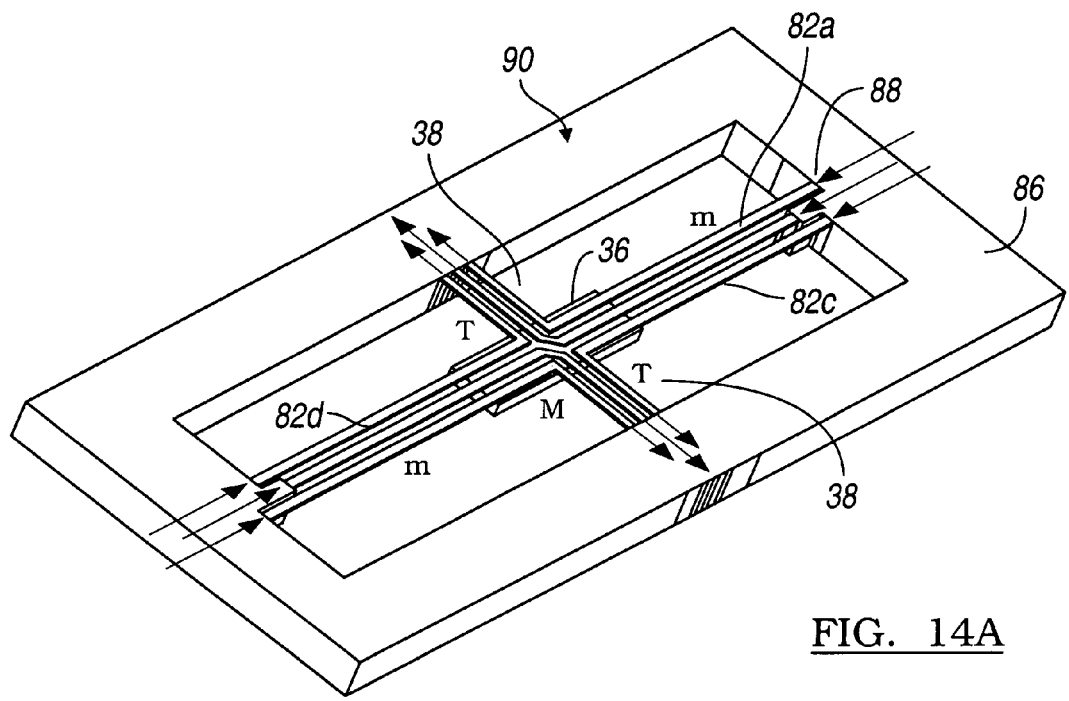
FIGS. 14A-14E represent an alternate sensor configured to measure the presence of a material in a fluid.
Figure 14B:
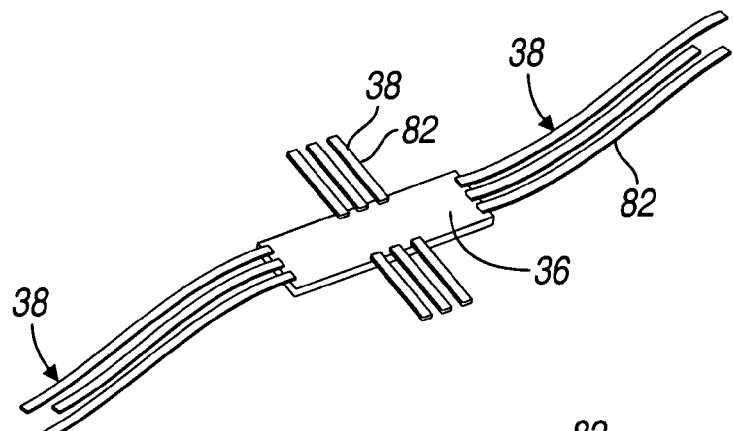
Figure 14C:
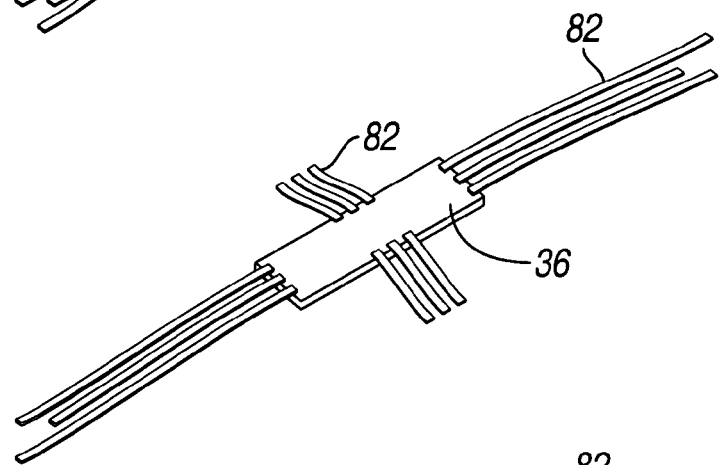
Figure 14D:
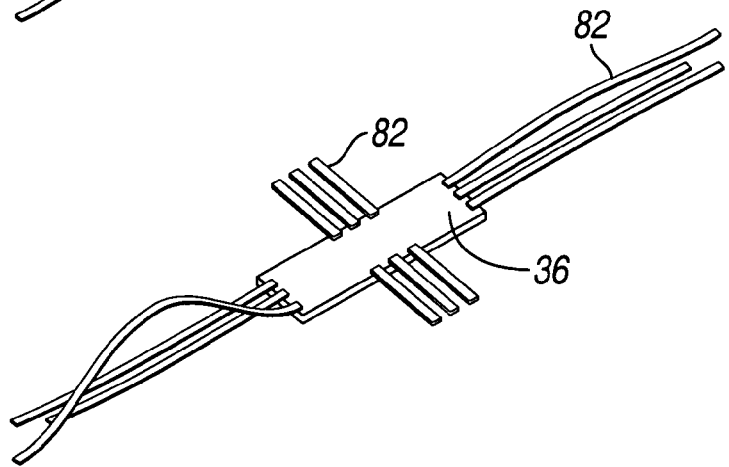
Figure 14E:
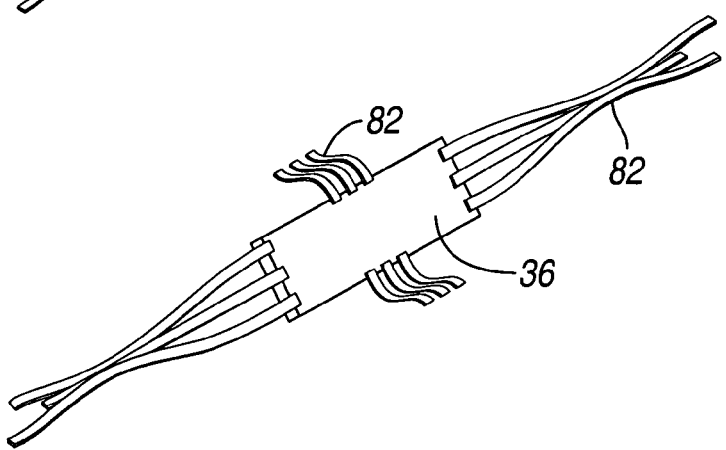
Figure 15:
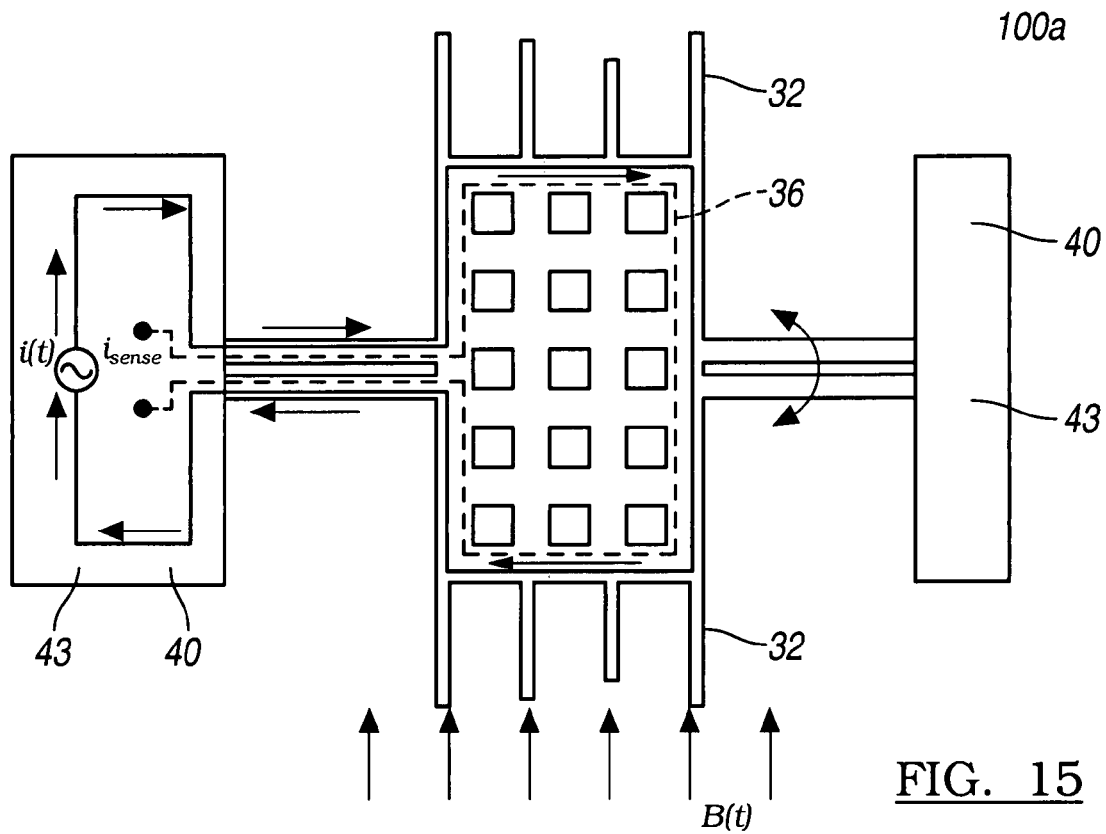
FIGS. 15-19 represent sensors driven by a magnetic field.
Figure 16:
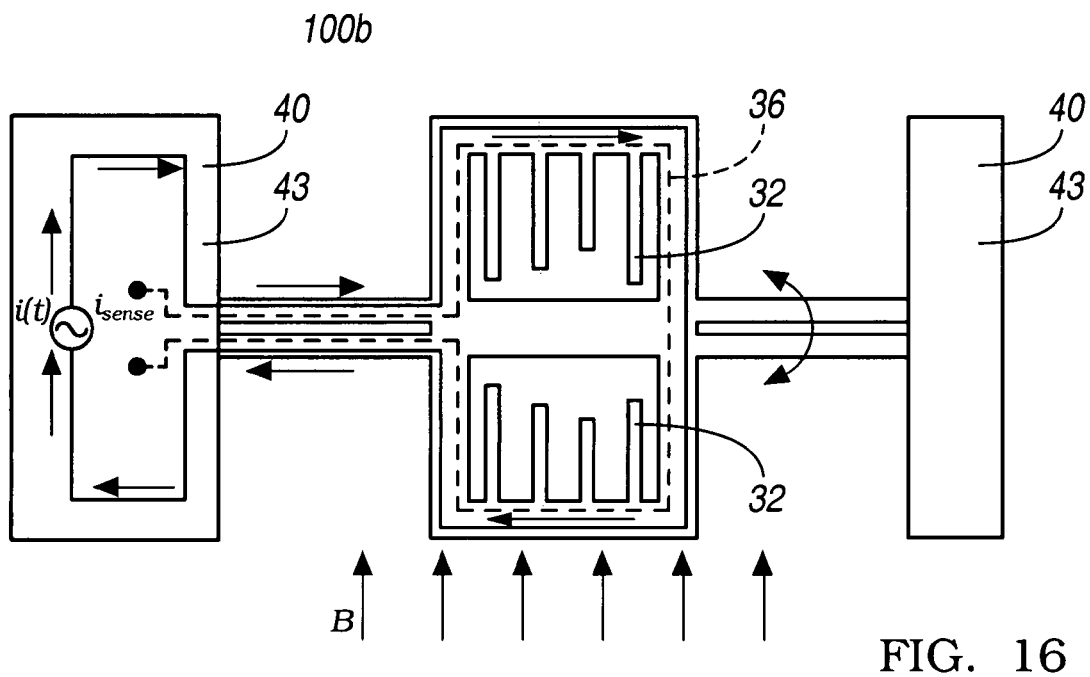
Figure 17:
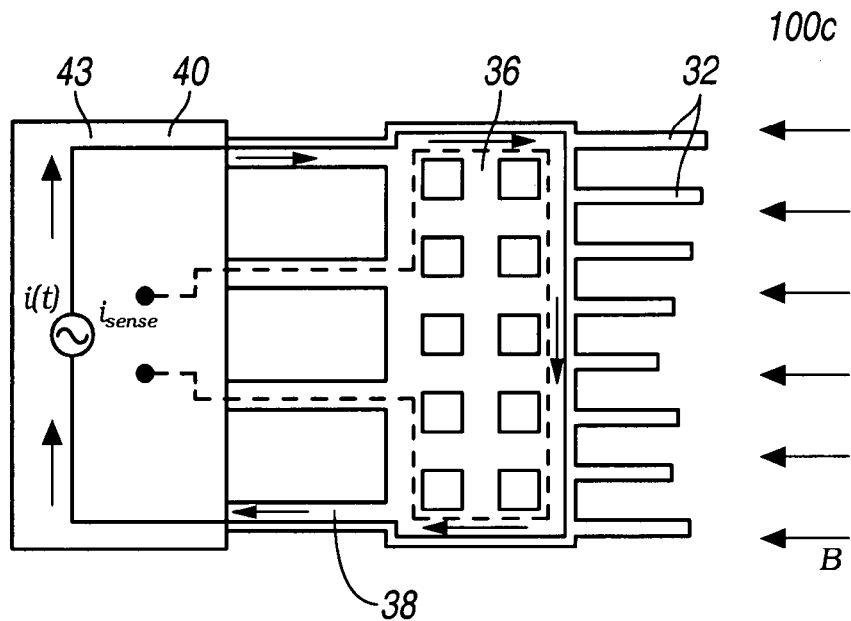
Figure 18:
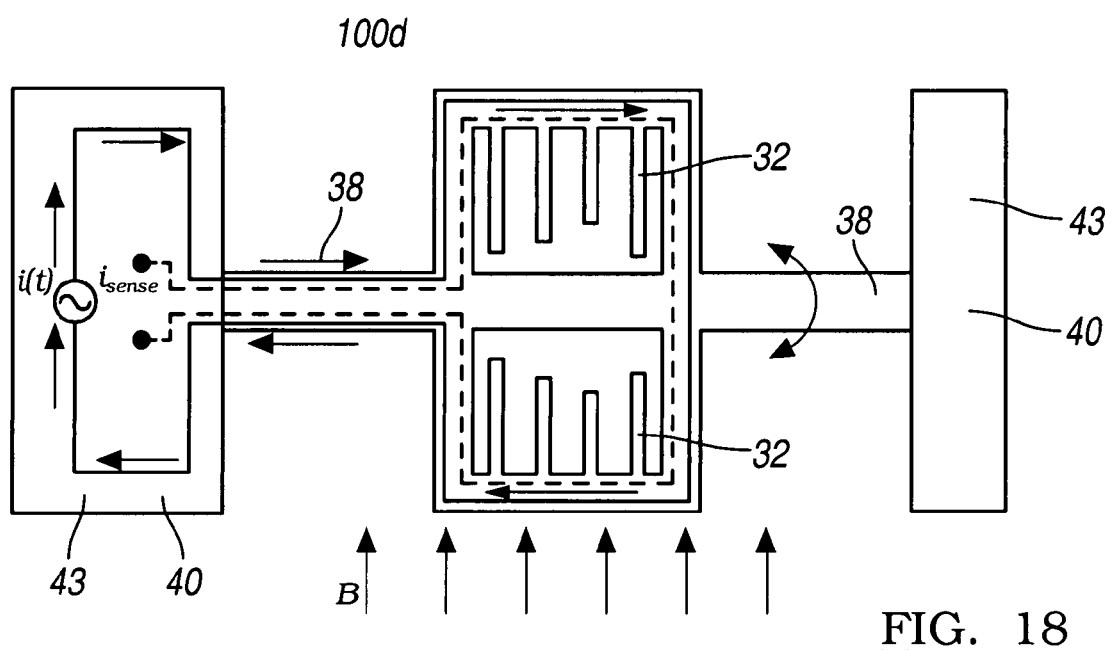
Figure 19:
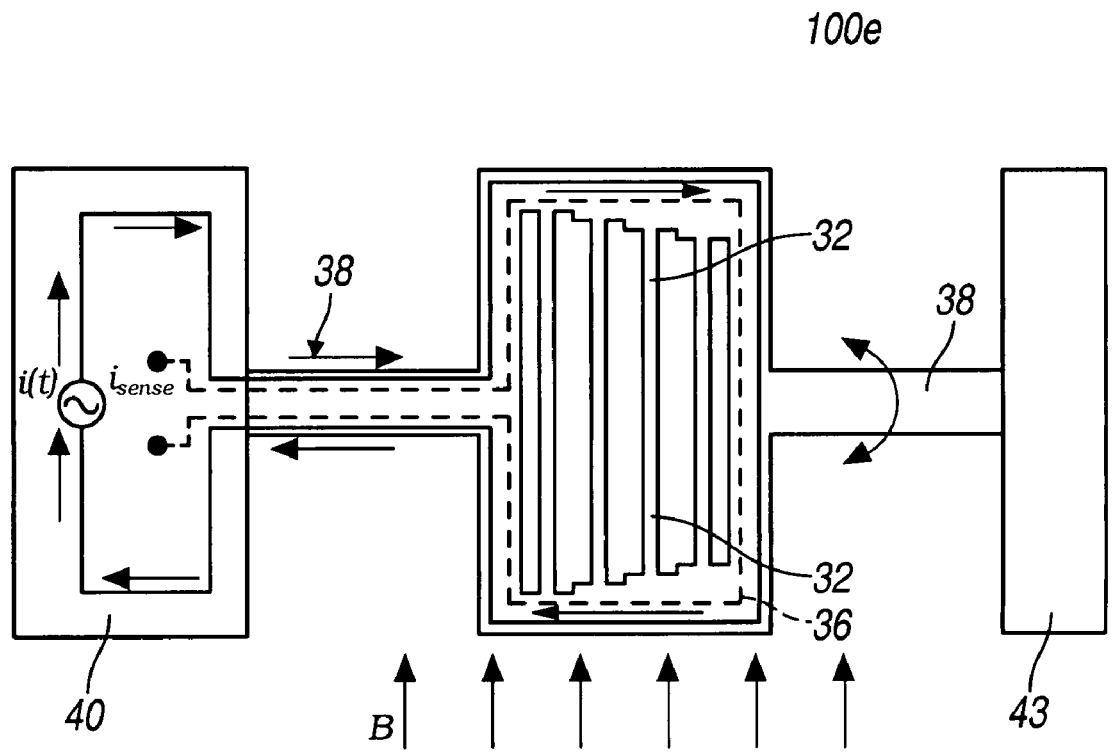

FIGS. 13 through 14E represent sensors 80 and 90. The sensors 80 and 90 are configured to detect the presence of analytes found within flowing fluids. In this regard, the sensors 80 and 90 have members 82 which define through bores 84a-84d which are configured to accept flowing fluids. Optionally, the sensing beams 82a-82d are mistuned, having varying lengths. These beams 82a-82d are coupled at a first end to the base 88 and to a second end at the shuttle mass 36. In the presence of an analyte, the stiffness or mass of the beams 82a-82d will change. It should be noted that the beams 82a-82d represent both support beams and detection beams. FIGS. 14B-14E represent multiple vibrational modes of the sensor 90 shown in FIG. 14A.

FIGS. 15-19 represent alternate sensors which are driven using the application of a constant magnetic field and an alternating current. Optionally, the sensors can be driven using a constant current and an alternating magnetic field. The sensors 100a-100e have a shuttle mass 36 coupled to ground using beams 38. The mass 36 has exterior or interior sensing beams 32. These beams 32 can be fixed at both ends (100e) or cantilevered (100a-100d).

To facilitate comparison between the device presented here and other resonant mass sensor designs, it is envisioned a number of pertinent sensor metrics can be modified to affect the sensor response. In the case of mass sensors, the most relevant metric is mass sensitivity, which is the smallest change in mass that can be accurately detected using a given sensor. For mass sensors 30 operating in a resonant mode, mass sensitivity is dependent on two independent metrics: mass responsivity and frequency resolution. The mass responsivity and frequency resolution. The mass responsibility of a system is a largely deterministic quantity that dictates how much the resonant frequency of a system changes with a small mass addition. Frequency resolution, on the other hand, quantifies the smallest frequency shift that can be measured in the presence of noise and uncertainty. In general, if frequency shifts are induced primarily through mass addition, the mass sensitivity, $\partial m$, of a resonant sensor can be approximated by $$\partial m \approx S^{-1} \partial \omega_0$$

where S is the mass responsivity and $\partial \omega_0$ is the system's frequency resolution. For the multi-degree-of-freedom sensor detailed here, however, this must be modified to account for N resonance shifts induced by up to N mass changes. This results in a mass sensitivity at the jth microbeam, $\Delta m_j$, which is approximated by $$\Delta m_j = S_{ij}^{-1} \Delta \omega_i \quad (12)$$

where $S_{ij}$ represents the i, j component of the mass responsivity matrix, which quantifies the shift in ith resonance of the system due to mass addition at the jth oscillator, and $\Delta \omega_i$ quantifies the frequency resolution associated with the Ah resonance.

Using the experimental results detailed in the previous section the mass responsivity matrix associated with the device shown in FIGS. 1a-1d can be partially compiled. For example, the mass responsivity associated with resonance (D) and a mass addition to the highest frequency microbeam can be computed to be 3.3 Hz/pg. Similarly, the mass responsivity associated with resonance (C) and a mass addition to the highest frequency microbeam can be computed to be approximately 0.1 Hz/pg. Continuing with these computations will reveal a diagonally dominant mass responsivity matrix. This can be attributed to the localized nature of the response, which, as detailed in the previous section, leads to significantly larger shifts in the resonances associated with the localized modes of the mass loaded microbeams 32a-32d.

Though the experimentally-determined mass responsivities reported above are comparable to other reported values for resonant multi-analyte sensors, they are significantly lower than those reported for sensors based on isolated microresonators. While much of this difference can be rectified through device scaling, it is important to note that the responsivities of the device presented here will always be slightly inferior to those of other microsensors. This can attributed to the inter-oscillator coupling, which manifests itself in the off-diagonal terms of the responsivity matrix, which leads to small shifts in each of the system's resonances, not just that associated with the localized mode of the altered beam. Current design studies are aimed at minimizing these off-diagonal terms while still allowing for the detection of resonance shifts using the shuttle mass' response.

Though the impact of thermomechanical noise, temperature fluctuations, absorption-desorption noise, and other effects known to contribute to a system's frequency resolution have been examined for isolated resonant microsensors (see, for example), the impact of these effects in coupled oscillator systems has thus far not been considered. Accordingly, present understanding facilitates, at best, a conservative estimate of the frequency resolution(s) associated with the sensor considered herein. For present purposes a frequency resolution of approximately 1 Hz is assumed. This results in a sub-picogram mass sensitivity.

However, if these changes prove insufficient, exploitation of alternative geometries, including in-plane torsional devices, and/or the coupled system's phase response may prove fruitful.

Mass addition can be realized via the deposition of a small platinum patch on one of the sensor's microbeams 32a-32d. In practice, however, resonance shifts typically arise from the accretion of a substance onto a functionalized, chemically-selective surface. In recent years, a considerable amount of research has focused on the development of chemically-active surfaces for use in microcantilever sensors. In the course of sensor development, these prior techniques can be adopted to functionalize cantilever surfaces with different chemicals (metals, polymers, etc.), thus allowing for the detection of multiple analytes using the SISO sensor.

While it is shown to adjust the resonant frequency of at least one component on the sensor, it is equally envisioned the changes in stiffness of these beams can be used to provide measurable changes to the resonant frequency of the sensor's microbeams 32a-32d.

What is claimed is:

1. A sensor comprising:
    a shuttle mass;
    first and second masses vibrationally coupled to the shuttle mass, the first mass having a first resonant frequency in the absence of a first analyte, and a second resonant frequency after the exposure to the first analyte; the second mass having a third resonant frequency in the absence of a second analyte, and a fourth resonant frequency after the exposure to the second analyte;
    a vibration sensor configured to detect a response of the shuttle mass; and
    an actuator configured to simultaneously drive the shuttle mass at a plurality of frequencies between a first predetermined frequency and a second predetermined frequency.
2. The sensor according to claim 1 wherein further comprising a circuit configured to detect changes in the response of the shuttle mass.

3. The sensor according to claim 1 wherein the vibration sensor comprises a plurality of charged members.

4. The sensor according to claim 1 wherein the actuator comprises a plurality of charged plates.

5. The sensor according to claim 1 wherein the first mass is a first cantilevered beam.

6. The sensor according to claim 5 wherein the second mass is a second cantilevered beam.

7. A sensor comprising:
a shuttle mass;
first and second beams vibrationally coupled to the shuttle mass, the first beam having a first resonant frequency in the absence of a first analyte, and a second resonant frequency after the exposure to the first analyte; the second beam having a third resonant frequency in the absence of a second analyte, and a fourth resonant frequency after the exposure to the second analyte;
a vibration sensor configured to detect vibration of the shuttle mass;
an actuator configured to simultaneously drive the shuttle mass at a plurality of vibrational frequencies.

8. The sensor according to claim 7 wherein the actuator is configured to impart a first vibrational frequency to the shuttle mass.

9. The sensor according to claim 8 wherein the actuator is configured to impart a second vibrational frequency to the shuttle mass.

10. The sensor according to claim 7 wherein the first beam comprises a first material configured to absorb the first analyte.

11. The sensor according to claim 10 wherein the second beam comprises a second material configured to absorb the second analyte.

12. A sensor comprising:
a support mass vibrationally coupled to a base;
first and second beams vibrationally coupled to the support mass, the first beam having a first resonant frequency in the absence of a first analyte, and a second resonant frequency in the presense the first analyte; the second beam having a third resonant frequency in the absence of a second analyte, and a fourth resonant frequency in the presence of the second analyte;
a vibration sensor configured to detect vibration of the support mass; and
an actuator configured to simultaneously drive the support mass at a plurality of frequencies.

13. The sensor according to claim 12 wherein the first beam comprises a first absorbing material and the second beam comprises a second absorbing material.

14. The sensor according to claim 12 wherein the actuator is configured to impart vibrational energy to the support mass.

15. The sensor according to claim 14 wherein the actuator is configured to impart a first frequency to the support mass.

16. The sensor according to claim 15 wherein the actuator is configured to impart a second frequency to the support mass.

17. A sensor comprising:
a support mass vibrationally coupled to a base;
first and second beams vibrationally coupled to the support mass, the first beam having a first resonant frequency in the absence of a first analyte, and a second resonant frequency in the presense the first analyte; the second beam having a third resonant frequency in the absence of a second analyte, and a fourth resonant frequency in the presence of the second analyte;
a vibration sensor configured to detect vibration of the support mass; and
an actuator configured to drive the support mass, wherein the first beam comprises a first material configured to absorb the first analyte, and wherein the second beam comprises a second material configured to absorb the second analyte, and wherein the support mass is coupled to the base through the first and second beams.

18. The sensor according to claim 17 wherein the first material comprises a detection material selected from the group consisting of silicon, polycrystalline silicon, amorphous silicon, polycrystalline diamond, amorphous diamond, gallium arsenide, silicon nitride, silicon carbide, titanium, gold, aluminum, aluminum nitride, nickel, silicon dioxide, glass, chromium, photoresist, platinum, titanium oxide, and combinations thereof.

19. The sensor according to claim 17 wherein the first and second beams are cantilevered beams.

20. A sensor comprising:
a sensing element having at least two vibrating members, each with a respective first resonant frequency, wherein the vibrating members are configured to exhibit a change in vibration response the presence of a plurality of analytes;
a drive element coupled to the sensing element, said drive element configured to apply force to the sensing element to simultaneously induce a vibration at a plurality of frequencies within the sensing element; and
a sensor configured to measure changes of a resonant frequency of at least one of the vibrating members.

21. The sensor according to claim 20 wherein one of mass or stiffness of a vibrating member changes in the presence of an analyte.

* * * * *

UNITED STATES PATENT AND TRADEMARK OFFICE
CERTIFICATE OF CORRECTION

| | | |
|---|---|---|
| PATENT NO. | : 7,584,649 B2 | Page 1 of 1 |
| APPLICATION NO. | : 11/809803 | |
| DATED | : September 8, 2009 | |
| INVENTOR(S) | : Steven W. Shaw et al. | |

It is certified that error appears in the above-identified patent and that said Letters Patent is hereby corrected as shown below:

Column 1, line 15, before "analyte", delete "an".

Column 2, line 30, "presense" should be --presence--.

Column 2, line 30, after "presence", insert --of--.

Column 5, line 15, "contract" should be --contrast--.

Column 7, line 43, "an" should be --can--.

Column 8, line 52, after "through", delete "at".

Column 8, line 59, "sensor" should be --sensors--.

Column 9, line 54, "Ah" should be --ith--.

Column 10, line 10, after "can", insert --be--.

Column 11, line 40, Claim 12, "presense" should be --presence--.

Column 11, line 40, Claim 12, after "presence", insert --of--.

Column 12, line 13, Claim 17, "presense" should be --presence--.

Column 12, line 13, Claim 17, after "presence", insert --of--.

Column 12, line 39, Claim 20, after "response", insert --in--.

Signed and Sealed this

Ninth Day of March, 2010

David J. Kappos
*Director of the United States Patent and Trademark Office*